United States Patent
Dowds et al.

(10) Patent No.: US 11,400,234 B2
(45) Date of Patent: *Aug. 2, 2022

(54) PATIENT-CONTACT ACTIVATED NEEDLE STICK SAFETY DEVICE

(71) Applicant: Safety Syringes, Inc., Franklin Lakes, NJ (US)

(72) Inventors: Philip E. Dowds, San Diego, CA (US); James M. Verespej, San Marcos, CA (US)

(73) Assignee: Safety Syringes, Inc., Franklin Lakes, NJ (US)

(*) Notice: Subject to any disclaimer, the term of this patent is extended or adjusted under 35 U.S.C. 154(b) by 361 days.

This patent is subject to a terminal disclaimer.

(21) Appl. No.: 16/401,557

(22) Filed: May 2, 2019

(65) Prior Publication Data
US 2019/0255258 A1    Aug. 22, 2019

Related U.S. Application Data

(63) Continuation of application No. 15/354,311, filed on Nov. 17, 2016, now Pat. No. 10,314,985, which is a continuation of application No. 13/290,937, filed on Nov. 7, 2011, now Pat. No. 9,526,846, which is a continuation-in-part of application No. 12/859,698, filed on Aug. 19, 2010, now abandoned.

(60) Provisional application No. 61/235,278, filed on Aug. 19, 2009.

(51) Int. Cl.
*A61M 5/32*    (2006.01)
*A61M 5/31*    (2006.01)

(52) U.S. Cl.
CPC .......... *A61M 5/326* (2013.01); *A61M 5/3129* (2013.01); *A61M 5/3202* (2013.01); *A61M 5/3204* (2013.01); *A61M 5/3272* (2013.01); *A61M 2005/3267* (2013.01)

(58) Field of Classification Search
CPC .. A61M 5/326; A61M 5/3129; A61M 5/3202; A61M 5/3204; A61M 5/3272; A61M 2005/3267
See application file for complete search history.

(56) References Cited

U.S. PATENT DOCUMENTS

| | | |
|---|---|---|
| 4,425,120 A | 1/1984 | Sampson et al. |
| 4,723,943 A | 2/1988 | Spencer |
| 4,813,940 A | 3/1989 | Parry |
| 4,826,490 A | 5/1989 | Byrne et al. |
| 4,834,717 A | 5/1989 | Haber et al. |

(Continued)

FOREIGN PATENT DOCUMENTS

| | | |
|---|---|---|
| DE | 10009484 A1 | 10/2001 |
| DE | 202004016791 U1 | 12/2004 |

(Continued)

*Primary Examiner* — Theodore J Stigell
(74) *Attorney, Agent, or Firm* — The Webb Law Firm

(57) ABSTRACT

A device that is used in conjunction with a needle-based medication injection device (e.g. a prefilled syringe) that prevents needle stick injuries. The used needle is shielded by a needle guard that surrounds and extends beyond the needle tip. In a preferred embodiment, before the needle is inserted into the patient, the needle guard projects forward to substantially hide visibility of the needle for safety and to reduce patient anxiety.

14 Claims, 27 Drawing Sheets

(56) References Cited

U.S. PATENT DOCUMENTS

| | | | |
|---|---|---|---|
| 4,887,998 A * | 12/1989 | Martin | A61M 25/0625 |
| | | | 604/110 |
| 4,894,055 A | 1/1990 | Sudnak | |
| 4,932,940 A | 6/1990 | Walker et al. | |
| 4,955,866 A | 9/1990 | Corey | |
| 4,976,701 A * | 12/1990 | Ejlersen | A61M 5/24 |
| | | | 206/365 |
| 5,013,305 A | 5/1991 | Opie et al. | |
| 5,085,639 A | 2/1992 | Ryan | |
| 5,104,384 A | 4/1992 | Parry | |
| 5,108,378 A | 4/1992 | Firth et al. | |
| 5,195,983 A | 3/1993 | Boese | |
| 5,201,708 A | 4/1993 | Martin | |
| 5,215,534 A | 6/1993 | De Harde et al. | |
| 5,232,458 A | 8/1993 | Chen | |
| 5,242,401 A | 9/1993 | Colsky | |
| 5,269,761 A | 12/1993 | Stehrenberger et al. | |
| 5,338,310 A | 8/1994 | Lewandowski | |
| 5,344,405 A | 9/1994 | Richards | |
| 5,358,491 A | 10/1994 | Johnson et al. | |
| 5,385,557 A | 1/1995 | Thompson | |
| 5,411,492 A | 5/1995 | Sturman et al. | |
| 5,472,430 A | 12/1995 | Vaillancourt et al. | |
| 5,562,624 A | 10/1996 | Righi et al. | |
| 5,573,513 A | 11/1996 | Wozencroft | |
| 5,582,597 A | 12/1996 | Brimhall et al. | |
| 5,591,138 A | 1/1997 | Vaillancourt | |
| 5,609,577 A | 3/1997 | Haber et al. | |
| 5,634,906 A | 6/1997 | Haber et al. | |
| 5,658,259 A | 8/1997 | Pearson et al. | |
| 5,688,241 A | 11/1997 | Asbaghi | |
| 5,795,336 A | 8/1998 | Romano et al. | |
| 5,833,670 A | 11/1998 | Dillon et al. | |
| 5,843,041 A | 12/1998 | Hake et al. | |
| 5,964,731 A | 10/1999 | Kovelman | |
| 6,077,245 A | 6/2000 | Heinrich et al. | |
| 6,099,504 A * | 8/2000 | Gross | A61M 5/2046 |
| | | | 604/140 |
| 6,110,147 A | 8/2000 | Perouse | |
| 6,186,980 B1 | 2/2001 | Brunel | |
| 6,379,336 B1 | 4/2002 | Asbaghi et al. | |
| 6,524,278 B1 | 2/2003 | Campbell et al. | |
| 6,530,905 B2 | 3/2003 | Asbaghi | |
| 6,537,257 B1 | 3/2003 | Wien | |
| 6,547,764 B2 | 4/2003 | Larsen et al. | |
| 6,565,540 B1 | 5/2003 | Perouse et al. | |
| 6,648,858 B2 | 11/2003 | Asbaghi | |
| 6,673,044 B2 | 1/2004 | Righi et al. | |
| 6,702,784 B1 | 3/2004 | Sheckler et al. | |
| 6,716,199 B2 | 4/2004 | DeHarde et al. | |
| 6,773,415 B2 | 8/2004 | Heiniger | |
| 6,800,066 B2 | 10/2004 | Targell | |
| 6,846,302 B2 | 1/2005 | Shemesh et al. | |
| 6,869,415 B2 | 3/2005 | Asbaghi | |
| 6,884,237 B2 | 4/2005 | Asbaghi | |
| 6,939,330 B1 | 9/2005 | McConnell-Montalvo et al. | |
| 6,958,055 B2 | 10/2005 | Donnan et al. | |
| 7,001,364 B1 | 2/2006 | Farhi | |
| 7,300,422 B2 | 11/2007 | Jouvin | |
| 7,540,858 B2 | 6/2009 | DiBiasi | |
| 7,666,164 B2 | 2/2010 | Giambattista et al. | |
| 7,699,813 B2 | 4/2010 | Liversidge | |
| 7,875,006 B2 | 1/2011 | Pessin | |
| 8,357,125 B2 | 1/2013 | Grunhut et al. | |
| 9,526,846 B2 * | 12/2016 | Dowds | A61M 5/3204 |
| 10,314,985 B2 * | 6/2019 | Dowds | A61M 5/3204 |
| 2001/0031949 A1 | 10/2001 | Asbaghi | |
| 2002/0004648 A1 | 1/2002 | Larsen et al. | |
| 2002/0004652 A1 | 1/2002 | Asbaghi | |
| 2002/0103461 A1 | 8/2002 | Asbaghi | |
| 2002/0173816 A1 | 11/2002 | Hung | |
| 2002/0193747 A1 | 12/2002 | Denolly | |
| 2003/0028171 A1 | 2/2003 | DeHarde et al. | |
| 2003/0120218 A1 | 6/2003 | Asbaghi | |
| 2003/0139705 A1 | 7/2003 | Larsen et al. | |
| 2004/0087875 A1 | 5/2004 | Asbaghi | |
| 2004/0111064 A1 | 6/2004 | Asbaghi | |
| 2004/0236283 A1 | 11/2004 | Tang | |
| 2005/0038391 A1 * | 2/2005 | Wittland | A61M 5/3202 |
| | | | 604/192 |
| 2005/0070854 A1 | 3/2005 | Wright | |
| 2005/0096598 A1 | 5/2005 | Crawford et al. | |
| 2005/0113750 A1 | 5/2005 | Targell | |
| 2005/0171485 A1 | 8/2005 | Larsen et al. | |
| 2005/0267410 A1 | 12/2005 | Koska | |
| 2005/0277893 A1 | 12/2005 | Liversidge | |
| 2006/0189933 A1 | 8/2006 | Alheidt et al. | |
| 2006/0264825 A1 | 11/2006 | Westbye et al. | |
| 2006/0270984 A1 | 11/2006 | Hommann | |
| 2007/0066936 A1 | 3/2007 | Lam | |
| 2007/0073224 A1 | 3/2007 | Dries | |
| 2007/0129674 A1 | 6/2007 | Liversidge | |
| 2007/0129686 A1 | 6/2007 | Daily et al. | |
| 2007/0129722 A1 * | 6/2007 | Cosmescu | A61M 39/1055 |
| | | | 606/42 |
| 2007/0151942 A1 | 7/2007 | Dishongh et al. | |
| 2007/0156101 A1 | 7/2007 | Liversidge | |
| 2007/0173772 A1 | 7/2007 | Liversidge | |
| 2007/0270759 A1 | 11/2007 | Pessin | |
| 2007/0287964 A1 | 12/2007 | Asbaghi | |
| 2008/0103453 A1 | 5/2008 | Liversidge | |
| 2008/0167624 A1 | 7/2008 | Weston et al. | |
| 2008/0200881 A1 | 8/2008 | Emmott et al. | |
| 2008/0300546 A1 | 12/2008 | Godara et al. | |
| 2009/0005742 A1 | 1/2009 | Liversidge | |
| 2009/0012478 A1 | 1/2009 | Weston | |
| 2009/0105663 A1 | 4/2009 | Brand et al. | |
| 2009/0204076 A1 | 8/2009 | Liversidge | |
| 2009/0227956 A1 | 9/2009 | Emmott et al. | |
| 2009/0326477 A1 | 12/2009 | Liversidge | |
| 2010/0016803 A1 | 1/2010 | Liversidge | |
| 2010/0036325 A1 | 2/2010 | Liversidge | |
| 2010/0063454 A1 | 3/2010 | Liversidge | |
| 2010/0076382 A1 | 3/2010 | Weston | |
| 2010/0152670 A1 * | 6/2010 | Low | A61M 5/3216 |
| | | | 604/198 |
| 2010/0160869 A1 | 6/2010 | Liversidge | |
| 2011/0098656 A1 | 4/2011 | Burnell et al. | |
| 2011/0319833 A1 | 12/2011 | Chun | |

FOREIGN PATENT DOCUMENTS

| | | |
|---|---|---|
| DE | 10339794 A1 | 4/2005 |
| DE | 102006041128 A1 | 3/2008 |
| DE | 102006041809 A1 | 3/2008 |
| EP | 0449907 A1 | 10/1991 |
| EP | 0559753 A1 | 9/1993 |
| EP | 0575492 A1 | 12/1993 |
| EP | 0813882 A2 | 12/1997 |
| EP | 0824923 A1 | 2/1998 |
| EP | 0864335 A2 | 9/1998 |
| EP | 1019123 A1 | 7/2000 |
| EP | 1032446 A1 | 9/2000 |
| EP | 1079878 A1 | 3/2001 |
| EP | 1128861 A2 | 9/2001 |
| EP | 1284769 A2 | 2/2003 |
| EP | 1285674 A1 | 2/2003 |
| EP | 1385564 A1 | 2/2004 |
| EP | 1452197 A2 | 9/2004 |
| EP | 1464352 A2 | 10/2004 |
| EP | 1473051 A2 | 11/2004 |
| EP | 1483004 A1 | 12/2004 |
| EP | 1485153 A2 | 12/2004 |
| EP | 1506740 A1 | 2/2005 |
| EP | 1605997 A1 | 12/2005 |
| EP | 1654020 A1 | 5/2006 |
| EP | 1660158 A1 | 5/2006 |
| EP | 1682206 A1 | 7/2006 |
| EP | 1755710 A1 | 2/2007 |
| EP | 1762261 A1 | 3/2007 |
| EP | 1814612 A2 | 8/2007 |
| EP | 1850894 A2 | 11/2007 |
| EP | 1949928 A1 | 7/2008 |
| EP | 1970086 A2 | 9/2008 |

(56) References Cited

FOREIGN PATENT DOCUMENTS

| | | |
|---|---|---|
| EP | 2022523 A1 | 2/2009 |
| EP | 2414398 A2 | 2/2012 |
| EP | 2930160 A1 | 10/2015 |
| EP | 2930161 A1 | 10/2015 |
| EP | 2930162 A1 | 10/2015 |
| JP | 2001521792 A | 11/2001 |
| JP | 2003511106 A | 3/2003 |
| JP | 2004504891 A | 2/2004 |
| JP | 2005520602 A | 7/2005 |
| JP | 2008246190 A | 10/2008 |
| JP | 2009509605 A | 3/2009 |
| JP | 2010540058 A | 12/2010 |
| SI | 0749758 T1 | 4/2003 |
| SI | 1928523 T1 | 11/2010 |
| WO | 8204293 A1 | 12/1982 |
| WO | 9111212 A1 | 8/1991 |
| WO | 9116993 A1 | 11/1991 |
| WO | 9605879 A1 | 2/1996 |
| WO | 9720538 A1 | 6/1997 |
| WO | 0006221 A1 | 2/2000 |
| WO | 0013727 A1 | 3/2000 |
| WO | 0027450 A1 | 5/2000 |
| WO | 0053244 A1 | 9/2000 |
| WO | 0108740 A1 | 2/2001 |
| WO | 0132253 A1 | 5/2001 |
| WO | 0142104 A1 | 6/2001 |
| WO | 0195805 A1 | 12/2001 |
| WO | 02074369 A1 | 9/2002 |
| WO | 02087669 A1 | 11/2002 |
| WO | 02089878 A1 | 11/2002 |
| WO | 02092160 A1 | 11/2002 |
| WO | 03105935 A2 | 12/2003 |
| WO | 2004028599 A2 | 4/2004 |
| WO | 2004028600 A1 | 4/2004 |
| WO | 2004041121 A2 | 5/2004 |
| WO | 2004052424 A2 | 6/2004 |
| WO | 2004096326 A1 | 11/2004 |
| WO | 2004101036 A1 | 11/2004 |
| WO | 2004105842 A1 | 12/2004 |
| WO | 2005004958 A1 | 1/2005 |
| WO | 2005011777 A1 | 2/2005 |
| WO | 2005030303 A1 | 4/2005 |
| WO | 2005051466 A1 | 6/2005 |
| WO | 2005079889 A1 | 9/2005 |
| WO | 2007077463 A1 | 7/2007 |
| WO | 2007099367 A1 | 9/2007 |
| WO | 2007143725 A2 | 12/2007 |
| WO | 2008034743 A1 | 3/2008 |
| WO | 2008035122 A1 | 3/2008 |
| WO | 2008044067 A1 | 4/2008 |
| WO | 2008050158 A2 | 5/2008 |
| WO | 2008075080 A1 | 6/2008 |
| WO | 2008111931 A1 | 9/2008 |
| WO | 2008127195 A1 | 10/2008 |
| WO | 2009040602 A1 | 4/2009 |
| WO | 2009040672 A2 | 4/2009 |
| WO | 2009095701 A1 | 8/2009 |
| WO | 2009102720 A1 | 8/2009 |
| WO | 2009114762 A1 | 9/2009 |
| WO | 2009114777 A1 | 9/2009 |
| WO | 2009144549 A1 | 12/2009 |

* cited by examiner

PATIENT-CONTACT ACTIVATED NEEDLE STICK SAFETY DEVICE

CROSS-REFERENCE TO RELATED APPLICATIONS

The subject application is a continuation of U.S. application Ser. No. 15/354,311 filed Nov. 17, 2016, which is a continuation of U.S. application Ser. No. 13/290,937 filed Nov. 7, 2011 (now U.S. Pat. No. 9,526,846), which is a continuation-in-part of U.S. application Ser. No. 12/859,698 filed Aug. 19, 2010, which claims the benefit of provisional application Ser. No. 61/235,278 filed Aug. 19, 2009, which applications are incorporated herein by reference.

FIELD

The following describes a device that is used in conjunction with a needle-based medication injection device (e.g. a prefilled syringe) that prevents needle stick injuries. The used needle is shielded by a cylindrical needle guard that surrounds and extends beyond the needle tip. In a preferred embodiment, before the needle is inserted into the patient, the needle guard projects forward to protect and substantially hide visibility of the needle to reduce patient anxiety.

BACKGROUND

The glass syringe and rubber stopper have for years provided an ideal drug storage closure having unique properties of impermeability to oxygen, low extractables, biocompatability, durability, etc. However, they are both formed by processes that do not lend themselves to tight geometrical tolerances. For instance, the syringe flange is formed when a glass tube is heated to a soft state and the edges pressed over to form an edge. Typical tolerances for the inside length of a syringe or the length of a stopper are both +/−0.5 mm. The finger flange thickness has a similar tolerance. Furthermore, tight tolerances were not originally needed by these devices because they were not used mechanically with other devices. Existing passive anti-needle stick safety devices for prefilled syringes must mount to the syringe but not interfere excessively with the force required to move the plunger rod during injection nor prevent the full travel of the plunger rod, which terminates when the stopper reaches the distal end of the inside of the syringe. The safety mechanism necessarily must be triggered toward the end of administration of the drug (near the end of the plunger rod travel). However, since virtually all safety devices locate the syringe against the safety device at a point under the syringe finger flange, a stack up of worst-case tolerances can put the required plunger rod travel variance at +/−1.5 mm, when considering the tolerances of the inside length of the syringe, syringe flange thickness, and stopper length (syringe manufacturers reference the syringe inside length from the proximal end of the syringe, not the distal underside of the finger flange). Accommodating the 3 mm plunger rod position variance is very difficult for safety devices and it is desirable to reduce and or eliminate any dependence of the safety device on the syringe and stopper tolerances.

SUMMARY

The present safety device described herein is directed to a needle guard for a syringe having the safety device triggering mechanism independent of the syringe and stopper tolerances. The present device is triggered when the needle guard body is displaced proximally relative to the device as the needle is inserted into the patient. The triggering point is broadly placed between point C and an angled step-down feature proximal to point C (FIG. 4A). As long as the needle guard body is displaced proximally a certain distance, the device will lockout, in a manner which is almost completely independent of the syringe or stopper geometry.

The present safety device also makes locking the needle shield completely contemporaneous with needle removal from the patient, reducing the possibility of needle stick injuries when, for instance, a patient suddenly jerks or flinches causing the needle to come out of the patient unexpectedly. Most commercially available needle safety devices require the plunger rod to be fully depressed in order to activate the safety mechanism.

Other systems, methods, features and advantages of the invention will be or will become apparent to one with skill in the art upon examination of the following figures and detailed description.

BRIEF DESCRIPTION OF THE FIGURES

The details of the invention, including fabrication, structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

DETAILED DESCRIPTION

Figure 1:
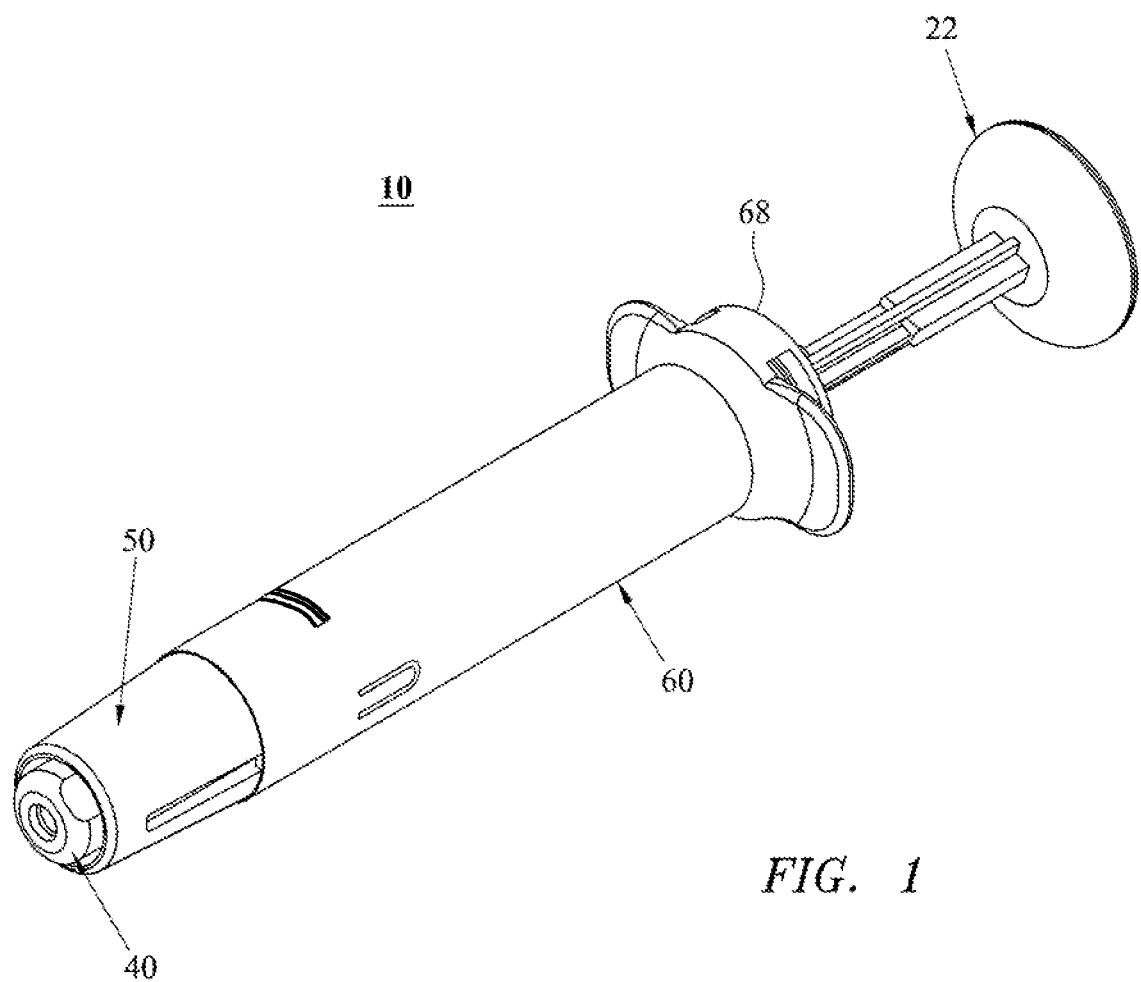
FIG. 1 illustrates the fully assembled device.
Figure 2:
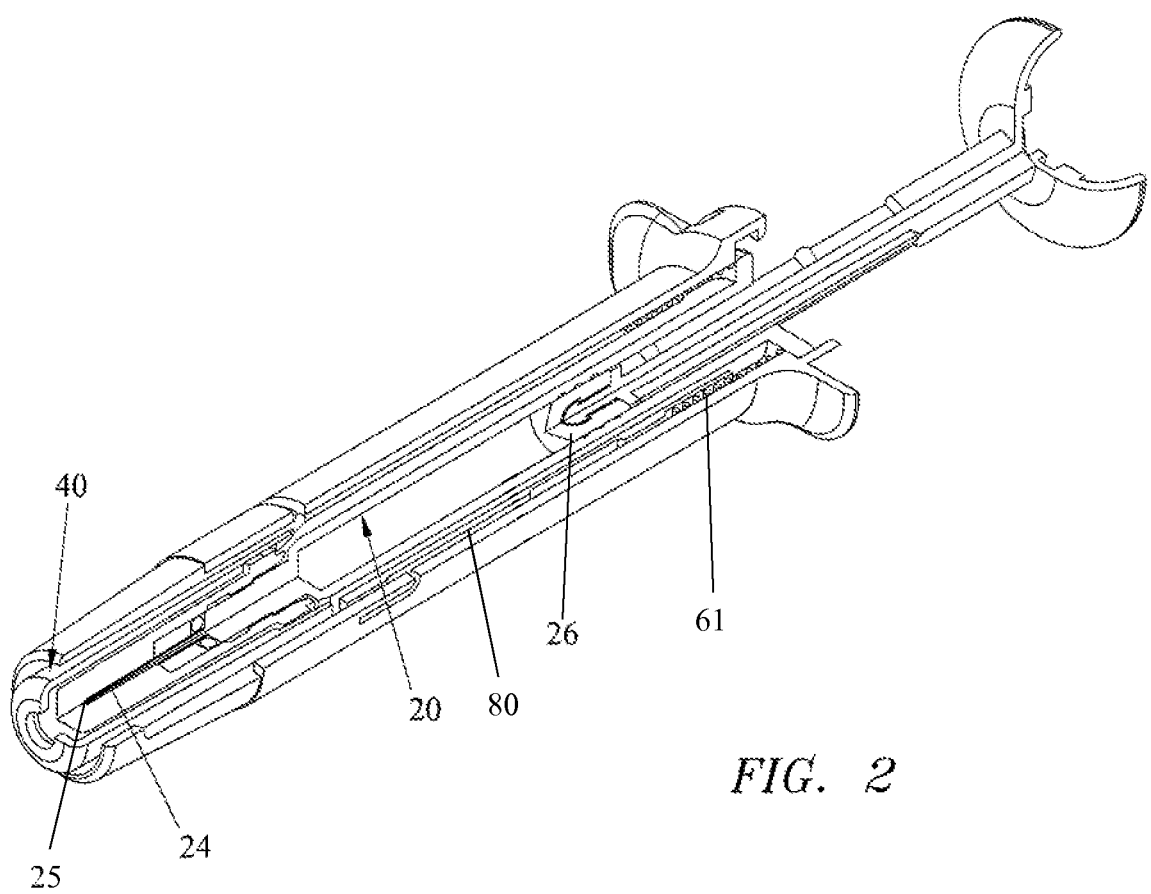
FIG. 2 illustrates the fully assembled device quarter section view.

The present safety device described herein is directed to a needle guard for a syringe having the safety device triggering mechanism independent of the syringe and stopper tolerances. The fully assembled safety device 10 is shown in FIG. 1. The assembly of the device 10 comprises a main body 60 with a plunger 22 emanating proximally from the proximal end 68 and a rigid needle shield (RNS) 40 and RNS removal tool 50 emanating distally from the main body 60. Inside the device 10, as shown in FIG. 2, is a prefilled syringe 20 with an attached needle 24 with the RNS 40 covering over the needle 24 to protect the needle and maintain a sterile barrier for the medication injection pathways. At the distal end of the assembly is the RNS removal tool 50, which is a removable covering over the RNS 40 that facilitates its removal just before injecting medication into the patient. The plunger 22 is attached to a syringe stopper 26. At the distal end of the assembly inside the main body 60 is the needle guard body 80, which is a tube that is concentric and interior to the main body 60 (see FIGS. 2, 3, 5, and 6).

Figure 3:
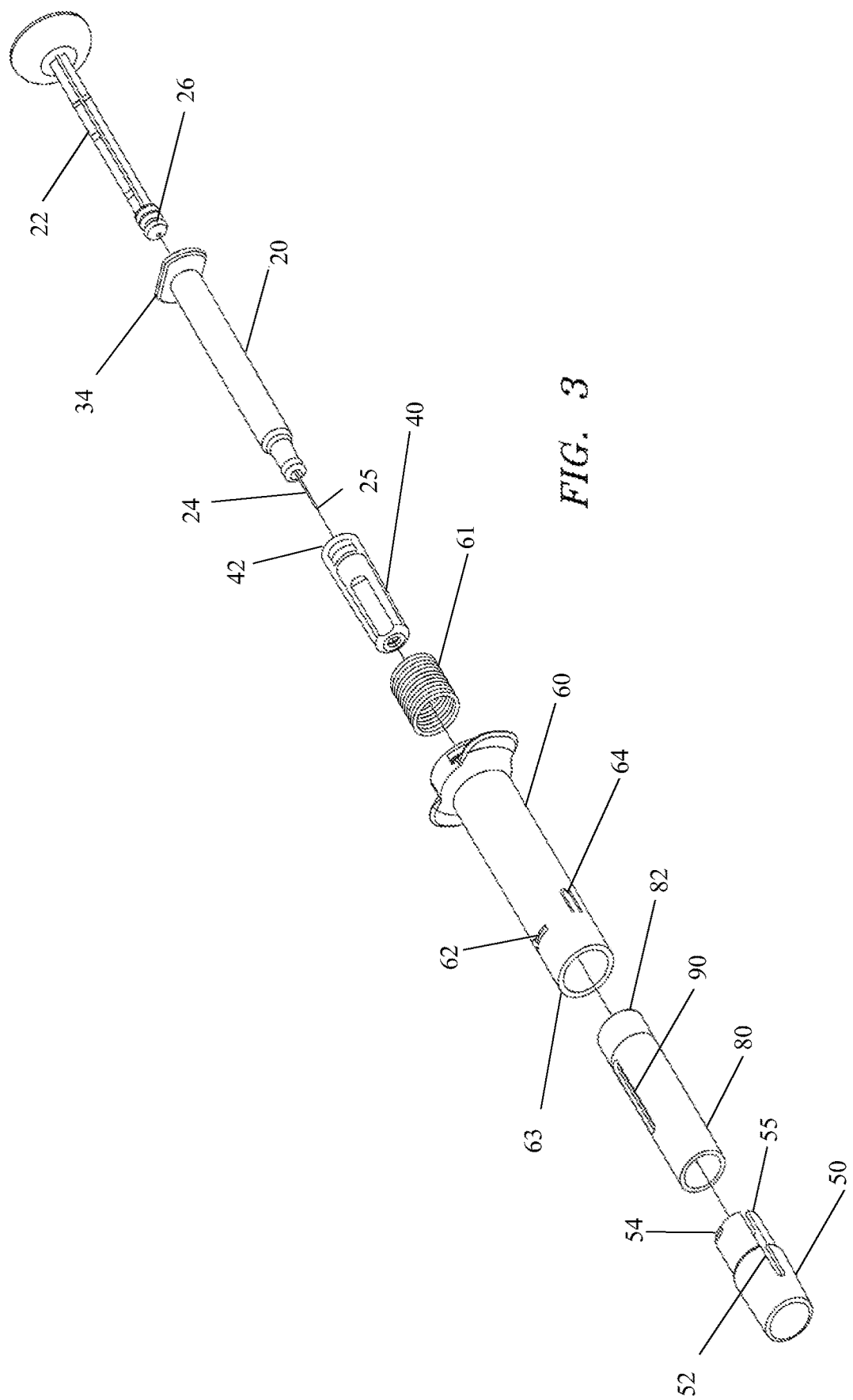
FIG. 3 illustrates the exploded view of the various components of the device.

As shown in FIGS. 2 and 3, the needle guard body 80 is axially slide-able with respect to the rest of the main body 60 and is biased in a distal direction by a compression spring 61 positioned between a syringe flange 34 and the needle guard body 80, and acting on a proximal end 82 of the needle guard body 80. Initially, the needle guard body 80 is held in a proximal position by the RNS removal tool 50. The RNS removal tool 50 is held in this position against the force of the spring 61 by retention barbs 54 that project outwardly at the proximal end 55 of the RNS removal tool 50 and that mate with corresponding retention windows 62 in the wall 63 of the main body 60 of the device 10 (see FIGS. 3, 5, 11, 13-16).

Figure 5:
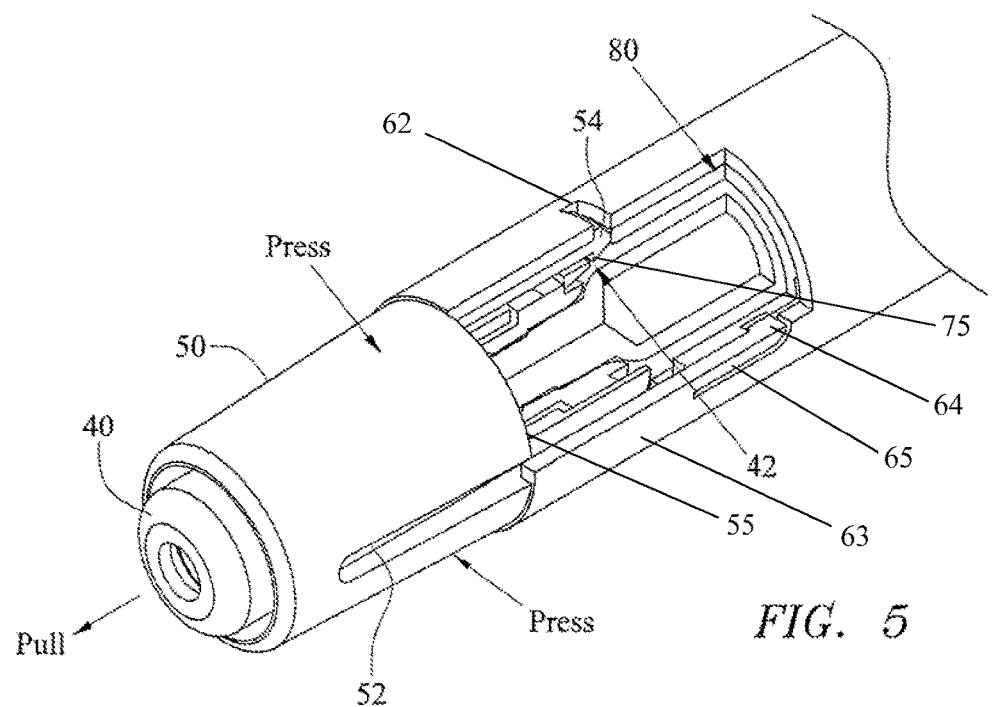
FIG. 5 illustrates the RNS removal tool. A section of the main body and needle guard body is removed for visualization of the RNS removal tool.

Immediately before injecting medication into a patient, the RNS 40, as depicted in FIG. 5, is removed by squeezing the RNS removal tool 50, which collapses along two slits 52 that run along the side of the tool 50 starting at its proximal end 55. The collapsed configuration of the tool 50 allows the retention barbs 54 at the proximal end 55 to disengage from the corresponding retention windows 62 in the main body 60 of the device 10. An inwardly projecting capture lip 75, at the proximal inside surface of the RNS removal tool 50, grasps the proximal edge 42 of the RNS 40, which in combination with the compressive force transmitted by the collapsed RNS removal tool 50 walls allows it to pull the RNS 40 from the distal end of the syringe 20 when the user pulls it in a distal direction (see FIGS. 5, 16 and 17).

Figure 4A:
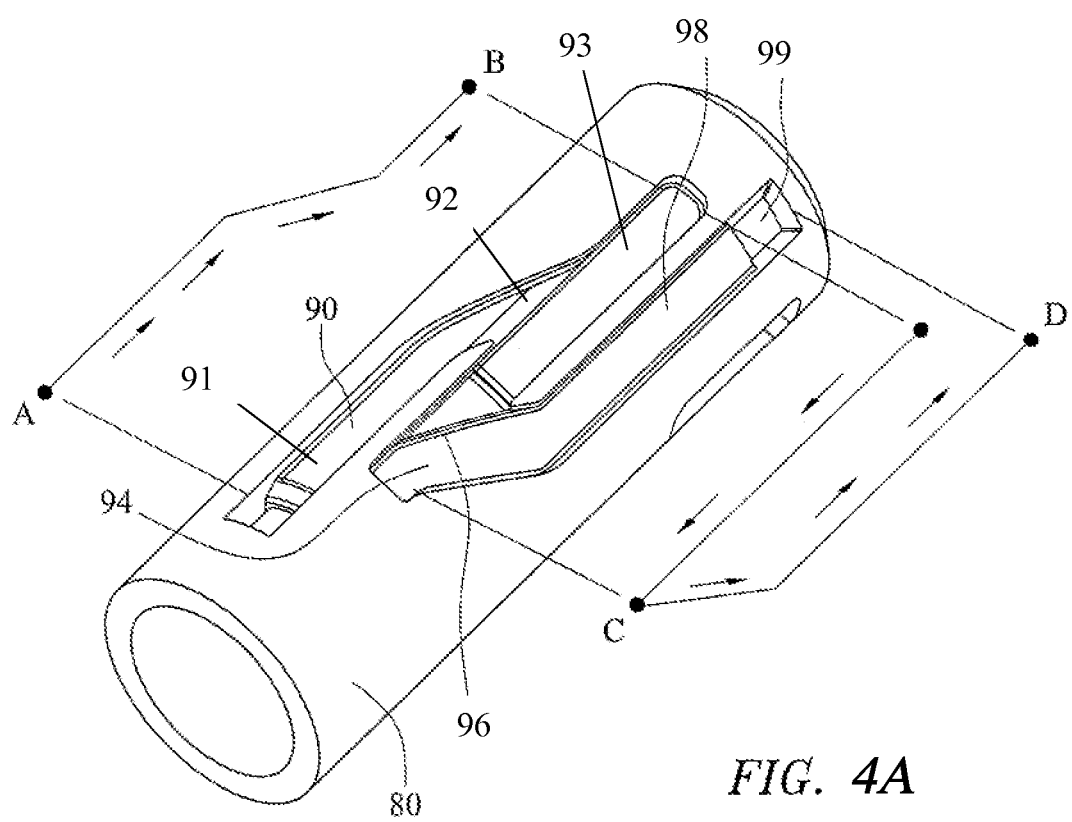
FIG. 4A illustrates the needle guard body grooves showing a position (A, B, C and D) of the main body protrusions during the steps of operating the device.
Figure 4B:
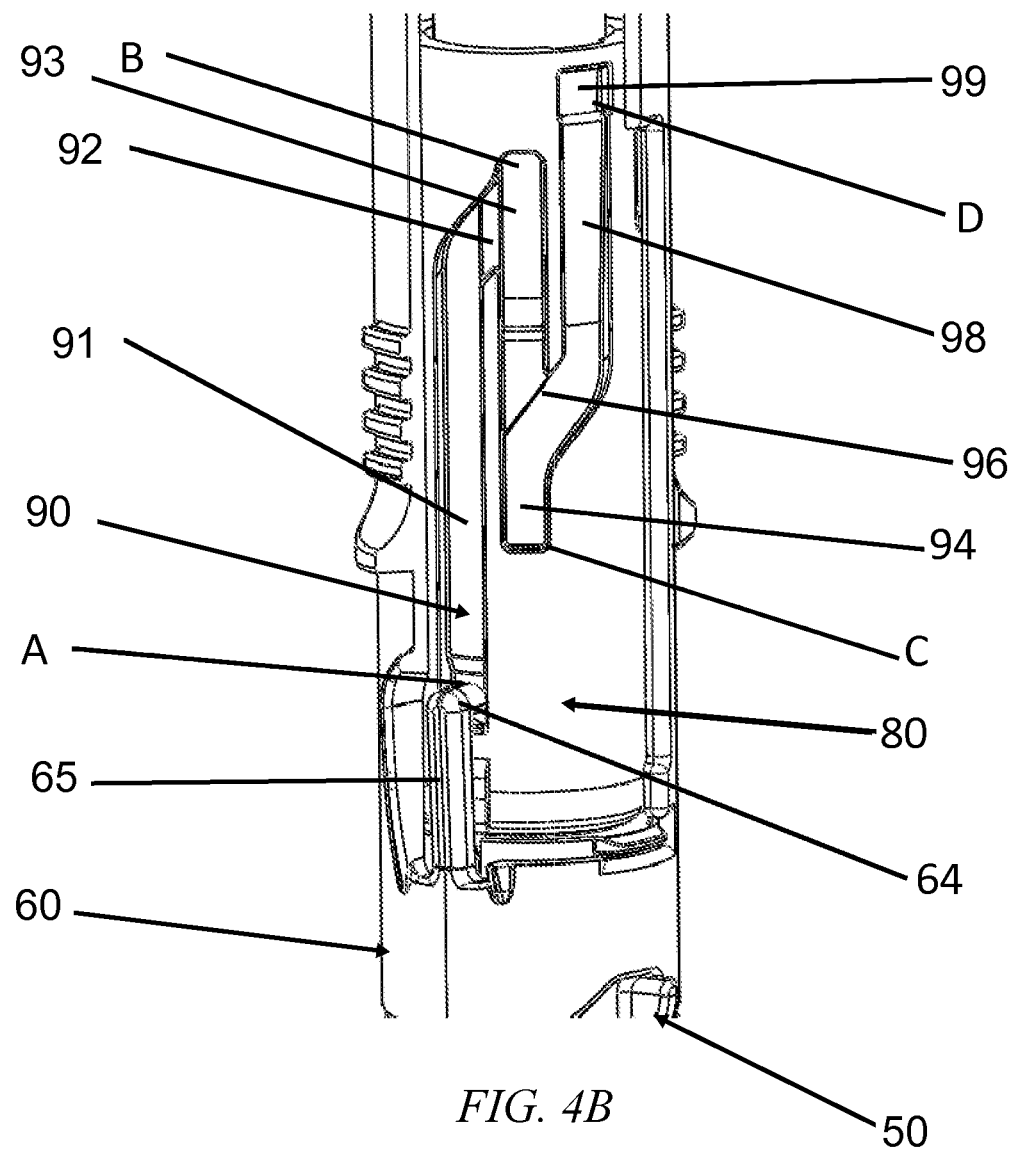
FIG. 4B illustrates the main body protrusion at position A of the needle guard body groove prior to removal of the rigid needle shield (RNS) and RNS removal tool. A section of the main body is removed for visualization of the needle guard body groove.
Figure 4C:
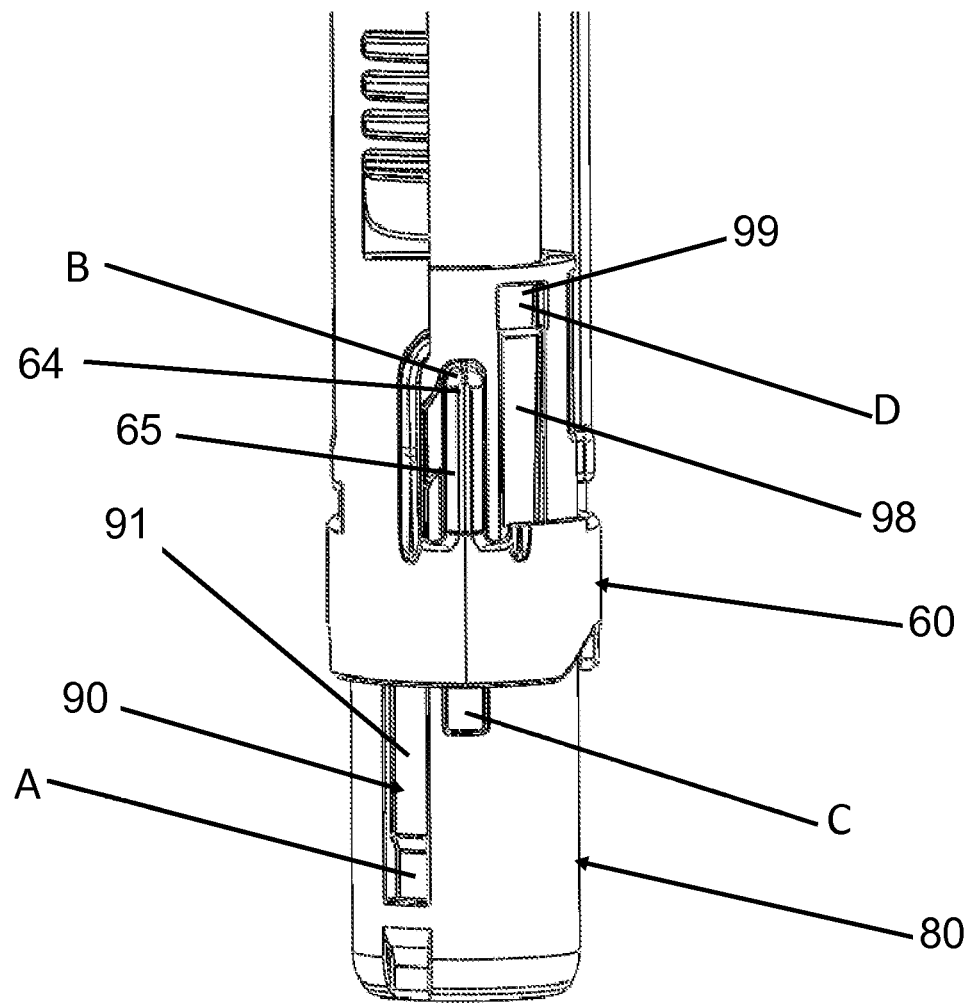
FIG. 4C illustrates the main body protrusion at position B of the needle guard body groove after the RNS and RNS removal tool have been removed. A section of the main body is removed for visualization of the needle guard body groove.
Figure 6:
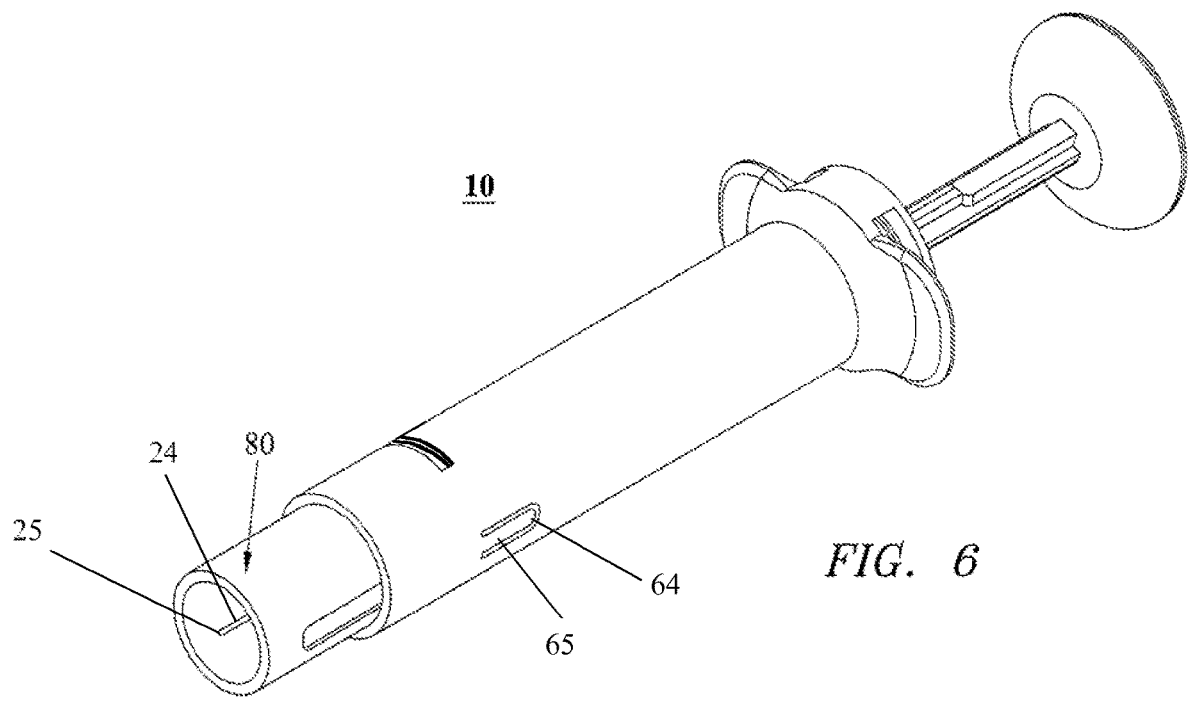
FIG. 6 illustrates the device ready for medication dispensing.

As the RNS removal tool 50 is withdrawn from the end of the device 10, the needle guard body 80 slides forward, as shown in FIG. 6, to an intermediate stop point B as shown in FIGS. 4A and 4C, governed by the interference between one or more inwardly projecting protrusions 64 from the main body 60 and corresponding grooves 90 in the outer surface of the needle guard body 80. The outer side of one protrusion 64 on the main body 60 is shown in FIG. 3, 4B-4E, 5 and 6. They are positioned at the end of cut-out sections that provide flexibility to the protrusions arms 65. The protrusions 64 interfere with the needle guard body grooves 90 by projecting into the groove space and controlling the movement of the needle guard body 80 against the distally directed force of the spring 61 and the proximally directed reaction force from the patient's skin.

Prior to removal of the RNS 40, the protrusion 64 is in position A of the needle guard body grooves 90 as shown in FIGS. 4A and 4B. After the RNS 40 is removed, the needle guard body 80 moves distally in response to the force of the spring 61, so that the protrusion 64 travels along a first groove section 91 to position B as shown in FIG. 4C. This includes some rotational movement of the needle guard body 80 as the protrusion 64 pushes against the angled wall of the first groove section 91 just before position B. This transition to position B includes a step 92 prior to groove deepening of the guard body groove 90 just prior to entering position B in a second groove section 93 to prevent the protrusion 64 from retracing its path back along the first groove section 91 toward position A.

As the needle 24 is inserted into the patient, the patient's skin pushes the needle guard body 80 proximally against the force of the spring 61, such that the groove protrusion 90-64 interface moves from position B along the second groove section 93 to position C as shown in FIG. 4A. Toward the distal end of the second groove section 93, the groove depth steps down to a fourth, deeper groove section 94 along an edge 96 that is angled to the axis of the needle guard body 80. At this point, the user must hold the device 10 against the skin working against the force of the spring 61 and perform the injection.

Figure 4D:
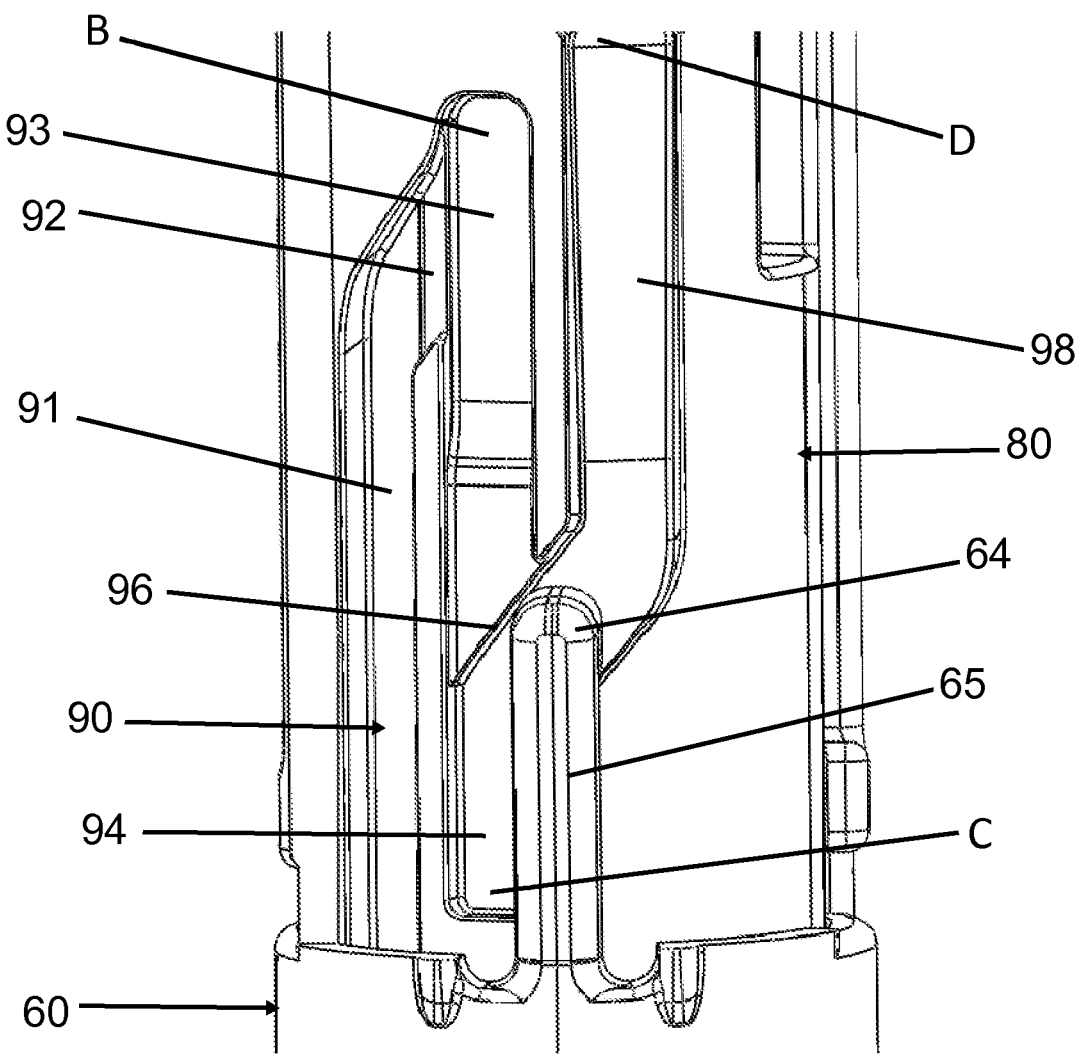
FIG. 4D illustrates the main body protrusion in transit between position C and D of the needle guard body groove. This would occur after the injection has taken place and the device is being withdrawn from the injection site. A section of the main body is removed for visualization of the needle guard body groove.
Figure 4E:
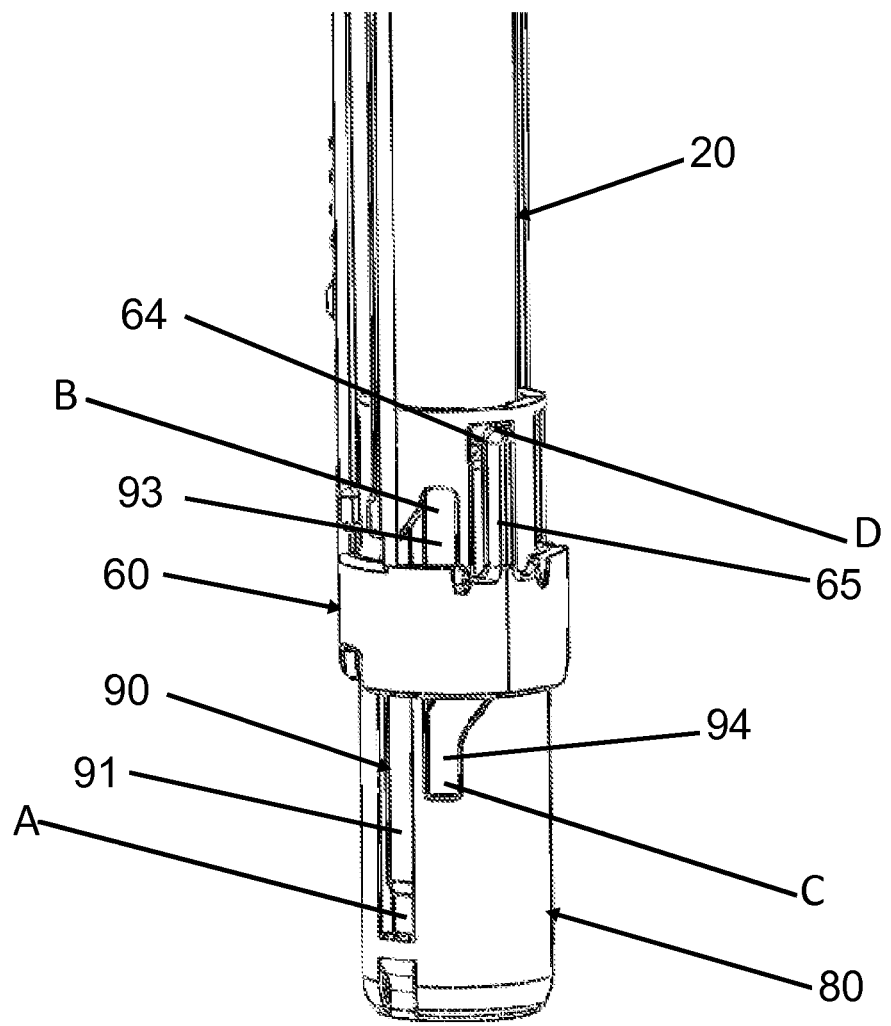
FIG. 4E illustrated the main body protrusion in position D of the needle guard body groove, in the locked out state. A section of the main body is removed for visualization of the needle guard body groove.
Figure 4F:
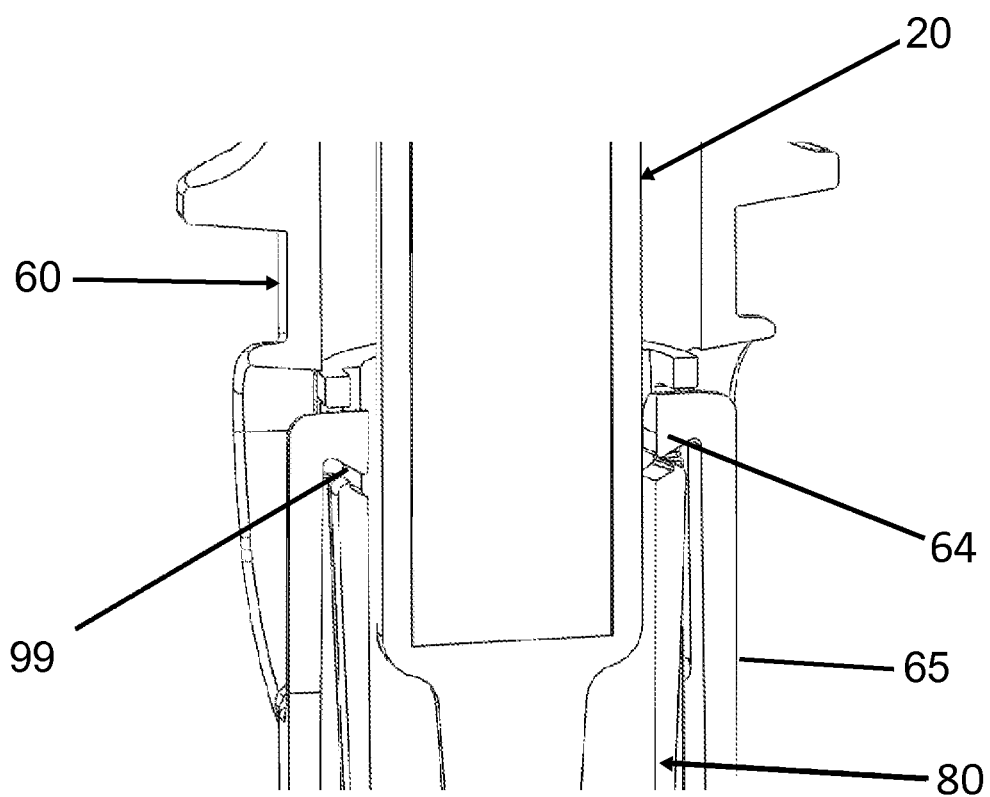
FIG. 4F illustrates a cross sectional view of the main body protrusions in position D of the needle guard body groove where the main body protrusion is substantially captured in a deepening of the groove to lock the device.

After the injection is complete and the device 10 is pulled away from the patient, the needle guard body 80 moves distally, as shown in FIG. 4D, under the force of the spring 61 from position C to position D with the protrusions 64 in the deeper groove section 94 such that the protrusions 64 encounter the stepped surface 96 causing the needle guard body 80 to rotate with respect to the main body 60 and enter a final groove section 98 in route to position D. As shown in FIGS. 4A, 4E and 4F, upon further distal movement of the needle guard body 80, the protrusion 64 drops into a further deepening of the groove 90 at a groove recess 99 such that the protrusion 64 is substantially captured in the groove recess 99 in a locked out state. This engagement prevents relative motion of the needle guard body 80 with respect to the main body 60.

As the needle guard body 80 moves from position C to position D as the needle 24 is pulled from the patient, it is projected distally around the needle 24 to the extent that it protects the caregiver and others from inadvertently being stuck by the needle tip 25. As shown in FIGS. 4E and 4F, the needle guard body 80 is held in this needle-shielding position by interference of the protrusions 64 in the groove recess 99 at position D so that the needle guard body 80 cannot be pushed proximally with respect to the main body 60, or pulled distally with respect to the main body 60.

For patients that have limited hand strength, holding the device against the skin while the needle 24 is in the injection site, requires maintaining a force against the spring 61 that pushes against the needle guard body 80 (position C in FIG. 4A). An alternative embodiment of the device to lessen this axial force could be accomplished by increasing the angle of the stepped surface 96 in the deeper groove section 94 that starts proximally to point C as shown in FIGS. 4A and 4D and deflects the main body protrusion 64 over to the straight groove section 98 that ends at position D. In FIGS. 4A and 4D, this angle is shown at about 45 degrees. An angle of perhaps 60 degrees would place a greater axial component of force against the spring force at some reduction of the lateral force. Of course, an angle of 90 degrees would hold the needle guard body 80 completely against the force of the spring 61 if the main body protrusion 64 could stay down in the deeper groove section 94, but there would be no lateral deflection to get the main body protrusion 64 over to position D where the device 10 locks out into the desired safety configuration. Depending on the coefficient of friction between the main body protrusion 64 and the needle guard body 80, the angle can be optimized to reduce the holding force for the patient, but still allow the main body protrusion 64 to lockout at position D shown in FIGS. 4A, 4E and 4F.

The sequence of steps to operate the device is described in FIGS. 5 through 10. First, as shown in FIG. 5, the RNS removal tool 50 is squeezed and pulled distally to remove the RNS 40 from the device. Squeezing the RNS removal tool 50 disengages the retention barbs 54 from the barb retention windows 62 and the capture lips 75 grip the proximal end of the RNS 40, thus removing the RNS 40 as the RNS removal tool 50 is pulled distally outward from the device. As a result of the removal of the RNS 40 and the RNS removal tool 50, the needle guard body 80 moves distally to the position shown in FIG. 6, under the force of the spring 61.

Figures 7, 8:
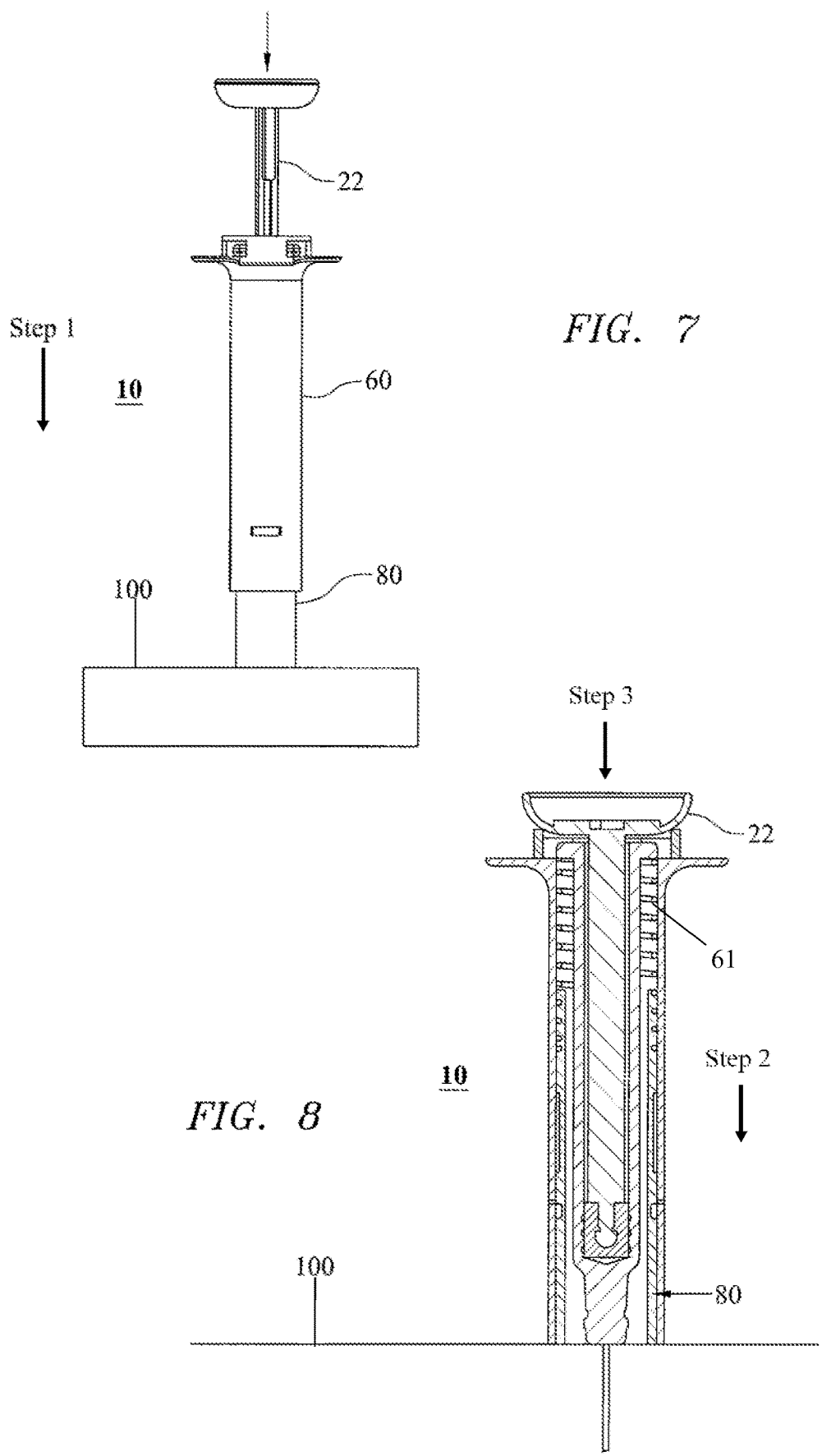
FIG. 7 illustrates first step of medication dispensing.
FIG. 8 illustrates medication dispensing steps and a cross section of the device after an injection of medication.

A composite of 3 steps to inject medication is shown in FIGS. 7 and 8. In Step 1, the needle guard body 80 is placed against the patient's injection site 100. In Step 2, the device 10 is pushed against the injection site 100, causing the needle guard body 80 to move proximally with respect to the main body 60 allowing the needle 24 to enter into the injection site 100. In Step 3, the plunger rod 22 is pushed forward to dispel the medication into the injection site 100. FIG. 8 also shows a cross-section of the device 10 with the needle guard 80 fully retracted and after the plunger 22 has been fully depressed.

Figure 9:
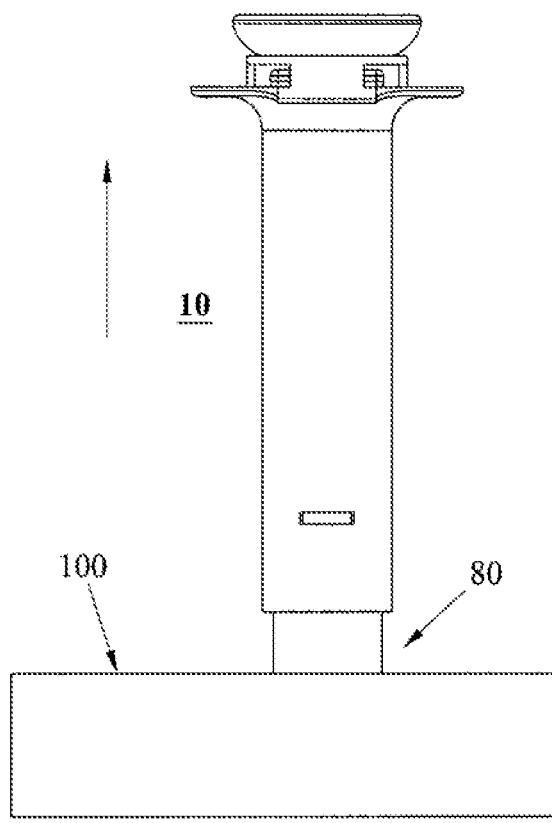
FIG. 9 illustrates removal of the device and needle from the injection site.
Figure 10:
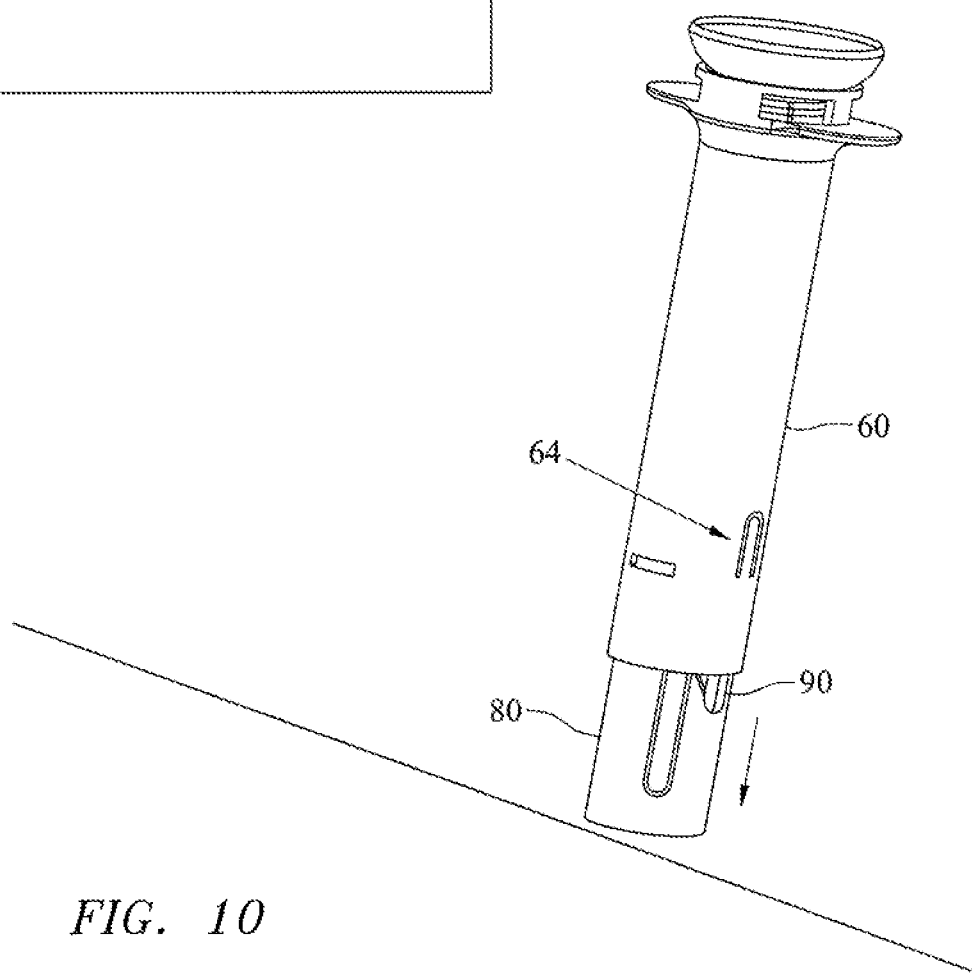
FIG. 10 illustrates the final safety configuration of the device.

In FIG. 9, the device 10 is being withdrawn from the injection site while the spring 61 pushes the needle guard body 80 distally. As the device 10 is fully withdrawn from the injection site 100, the needle guard body 80 fully extends forward as shown in FIG. 10. At this point the main body protrusions 64 have entered position D in the groove 98 of the needle guard body 80 as shown in FIGS. 4E and 4F and locked the needle guard body 80 from further motion with respect to the main body 60 to prevent any needle sticks.

To facilitate movement of the main body 60 and its protrusions 64 with respect to the grooves 90 of the needle guard body 80, one or both components can be made using a plastic resin with ample lubrication (e.g. high content of mold release). Alternatively, dissimilar plastic resins exhibiting a low mutual coefficient of friction can be used for the components.

It is to be understood that there exist alternative arrangements of components that would still fall within the scope of what is described and claimed within this application. For instance, the needle guard body 80 could be positioned on the outside of the main body with interior-facing grooves and outwardly facing protrusions on the main body 80.

Figure 11:
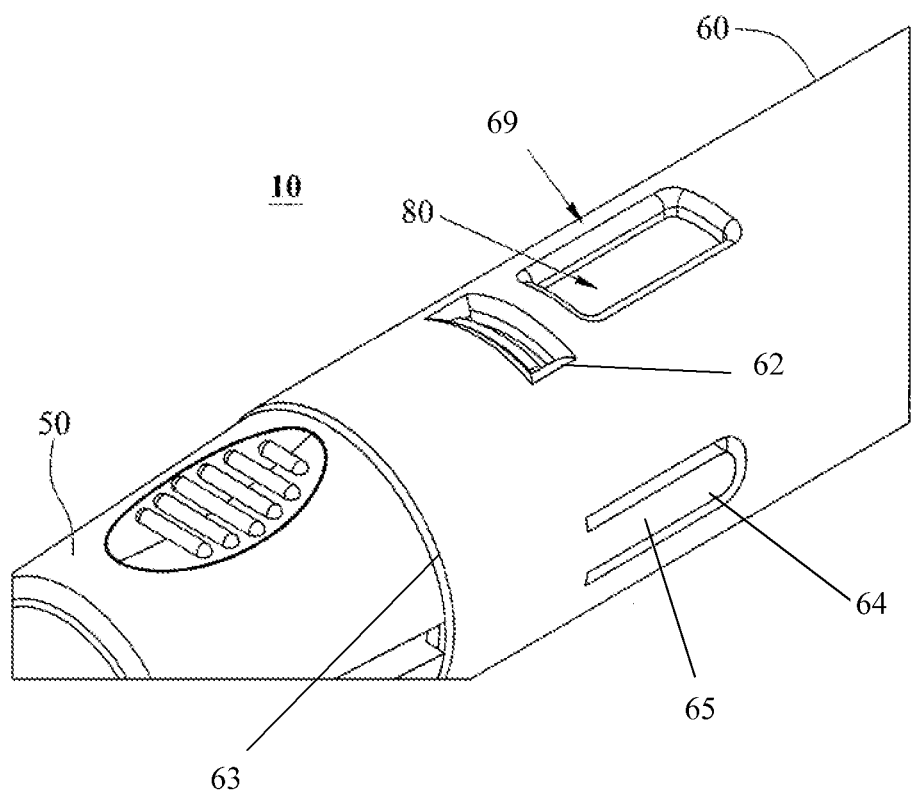
FIG. 11 illustrates the main body window position prior to the removal of the RNS and RNS removal tool.
Figure 12:
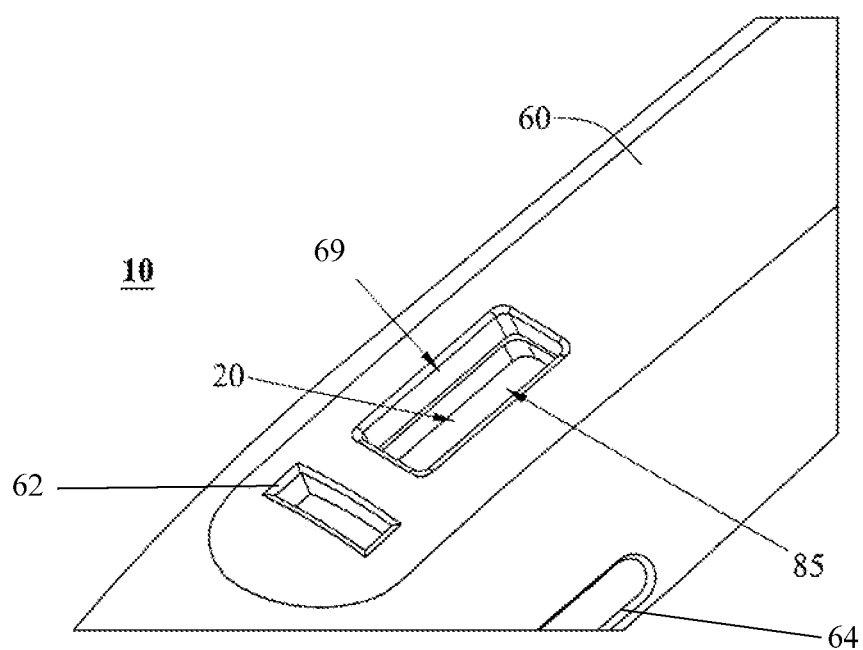
FIG. 12 illustrates the main body window and needle guard body window position after the RNS and RNS removal tool have been removed and the needle guard body has moved forward.

An alternative embodiment for the safety device is presented for use with light-sensitive drugs that require only minimal exposure to light. In this embodiment, the components of the device are made of opaque materials (e.g. plastic resins with pigments, tinted glass, etc.) that effectively block light from reaching the drug in the medication delivery device. However, drug injection instructions normally require the caregiver to inspect the drug to check that it is not cloudy, etc. prior to giving the injection. To achieve this, as shown in FIGS. 11 and 12 the main body 60 and needle guard body 80 of the device 10 have diametrically opposed windows that are positioned with respect to each other such that they are not aligned until the RNS removal tool 50 and RNS 40 have been removed. After removal, when the diametrically opposed windows on the two components align, as shown in FIG. 12, they form a line of sight through the device 10, which enables the caregiver to inspect the drug volume. Referring to FIG. 11, prior to the removal of the RNS 40 and RNS removal tool 50, the main body window 69 is blocked internally by the outer surface of the opaque needle guard body 80. In FIG. 12, after the RNS 40 has been removed and the needle guard body 80 has moved forward, the window 69 of the main body 60 is aligned with the window 85 of the opaque needle guard body 80 allowing visibility into the syringe 20. A similar window is provided on the diametrically opposite side of the device 10.

The RNS 40, RNS removal tool 50, and plunger rod 22 components would also be made of opaque materials to prevent light exposure at the ends of the device 10. A covering (not shown) over the proximal end of the syringe with a hole for the plunger rod could also be created to provide additional light protection. Similarly, a second cover (158; see FIG. 18A) could be placed over the distal end of the RNS removal tool to block light from entering the distal end.

Figure 13:
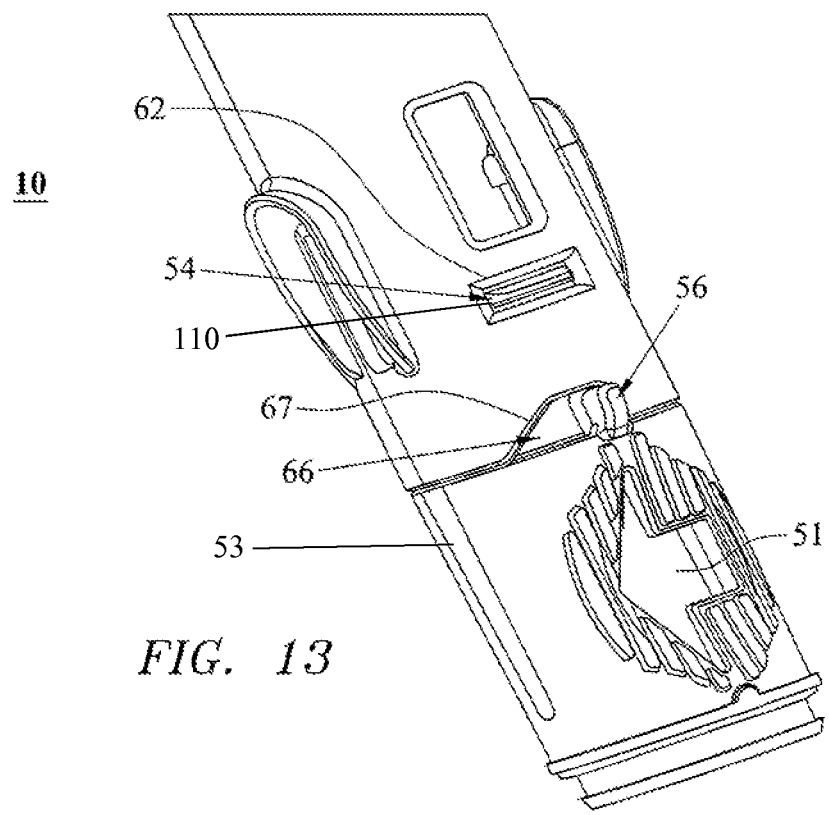
FIG. 13 illustrates an alternative embodiment of the RNS removal tool.
Figure 14:
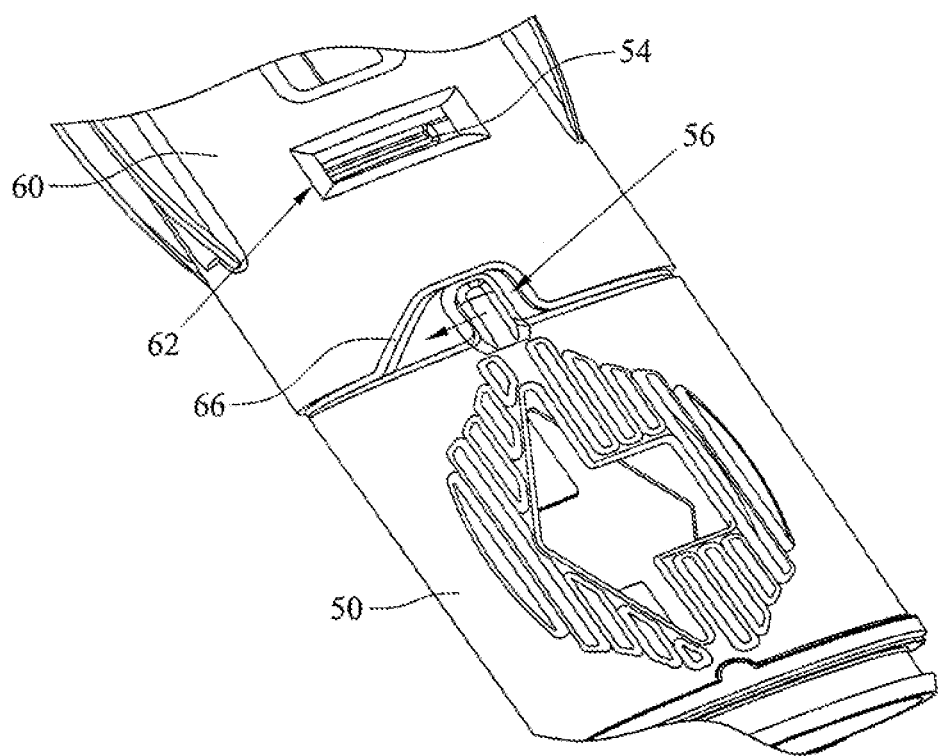
FIG. 14 illustrates the RNS removal tool radial cam mechanism, which acts to engage or grasp the RNS upon initial rotation.
Figure 17:
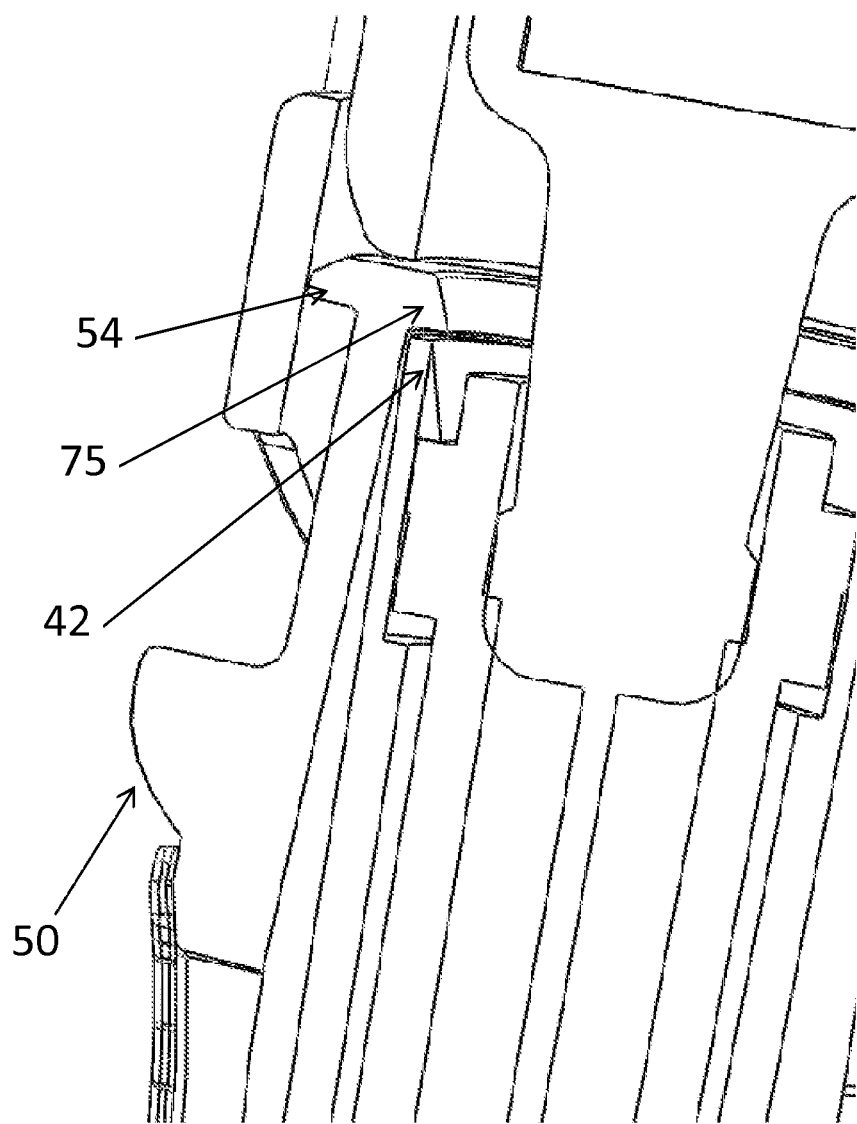
FIG. 17 illustrates the removal tool retention barb engaging proximal end of the RNS.

The RNS 40 not only protects the needle 24 from being bent or its tip 25 from being damaged but it also forms one of the sterile barriers for the drug closure system. It must perform these functions before, during, and after sterilization and is therefore a complicated component that receives a tremendous amount of testing during the drug development and approval process. Since it has potential contact with the drug inside the syringe 20, it becomes part of the specific drug closure system that receives regulatory approval and is therefore difficult to change after approval. They have become industry standard devices produced by specialized third party manufacturers. Nevertheless, they have limitations and deficiencies, namely that they can become difficult to remove from the syringe 20 after sterilization and storage, often requiring greater than 20 N of force to remove. On a small part (approximately 0.25 inches in diameter, 1 inch long) such as this, it makes it difficult for healthcare workers to remove due to the small grasping area. Patients that perform self-administration, especially those with limited manual dexterity or strength (e.g. arthritic or multiple sclerosis patients) will find it extremely difficult to remove. Therefore, an added improvement of the present device 10 is to facilitate the RNS 40 removal. This is accomplished by the RNS removal tool 50, which, as shown in FIGS. 13, 14, 15, 23 and 24, in addition to presenting a bigger surface area with which the user can grab, it also features some cam mechanisms to provide mechanical leverage in removing the RNS 40. As depicted, the RNS removal tool retention barbs 54 reside inside the main body barb retention window 62 before the RNS 40 is removed. The lateral sides 110 of the barb 54 and the corresponding edges of the main body barb retention window 62 are angled, as shown in FIG. 13, such that as the RNS removal tool 50 is rotated, the barbs 54 push against the edge of the window 62 and are deflected radially inward as shown in FIGS. 14 and 17. The axial cam follower 56 on the RNS removal tool 50, as shown in FIG. 14, has not yet acted against the main body axial cam profile 66.

Figure 15:
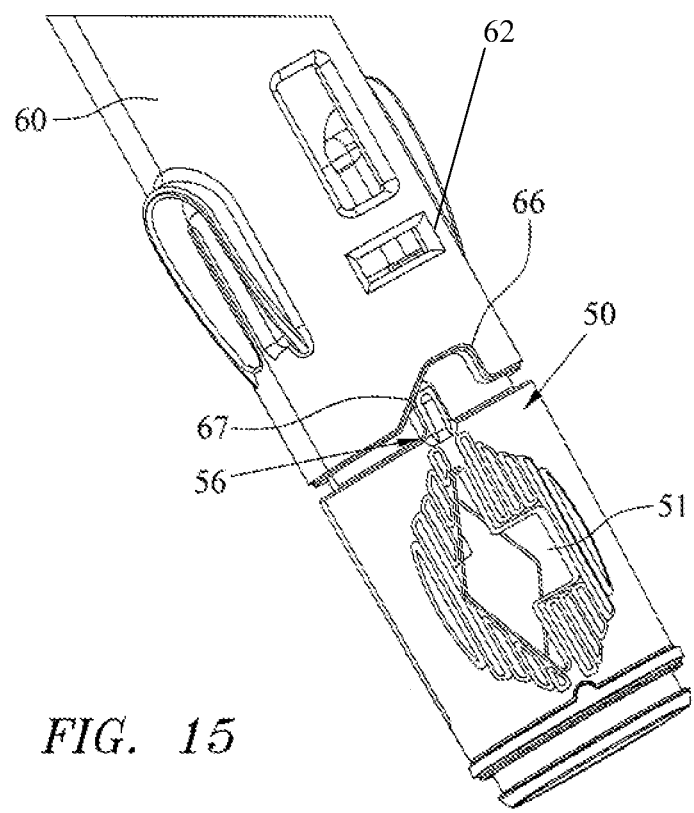
FIG. 15 illustrates the RNS removal tool axial cam mechanism, which acts to pull the RNS from the syringe in an axial direction.
Figure 16:
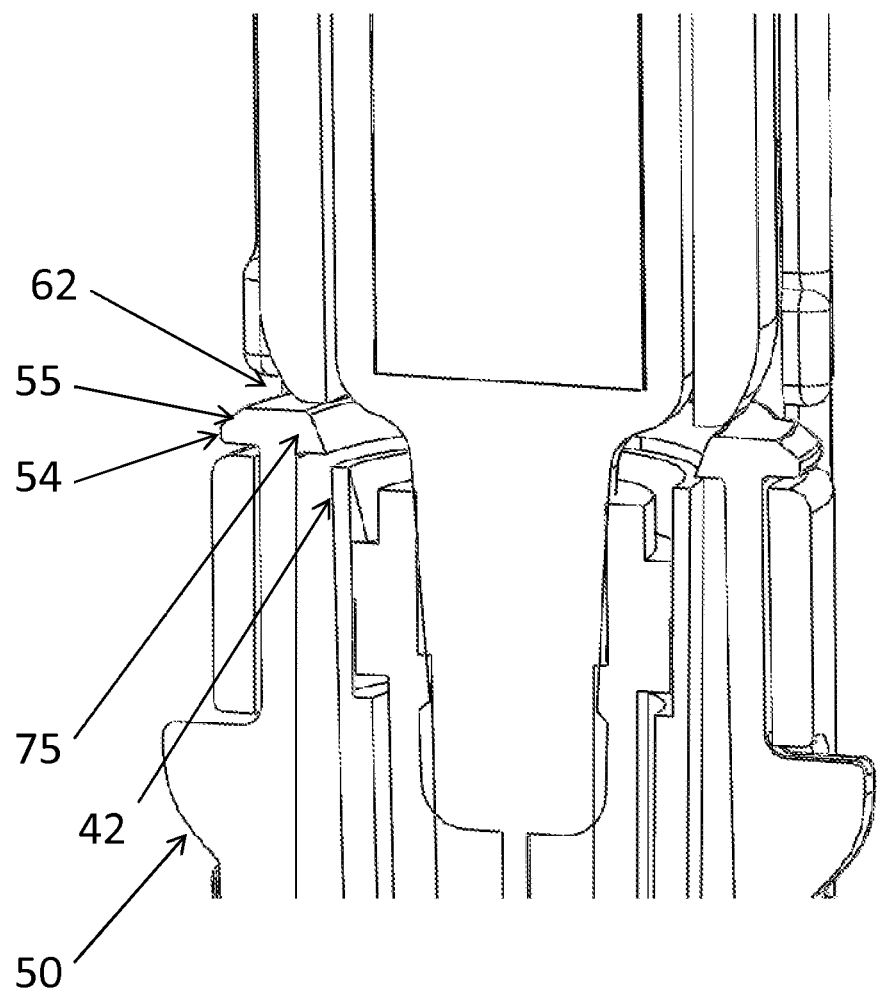
FIG. 16 illustrates the nominal orientation of the RNS removal tool retention barb, allowing syringe assembly.
Figure 22:
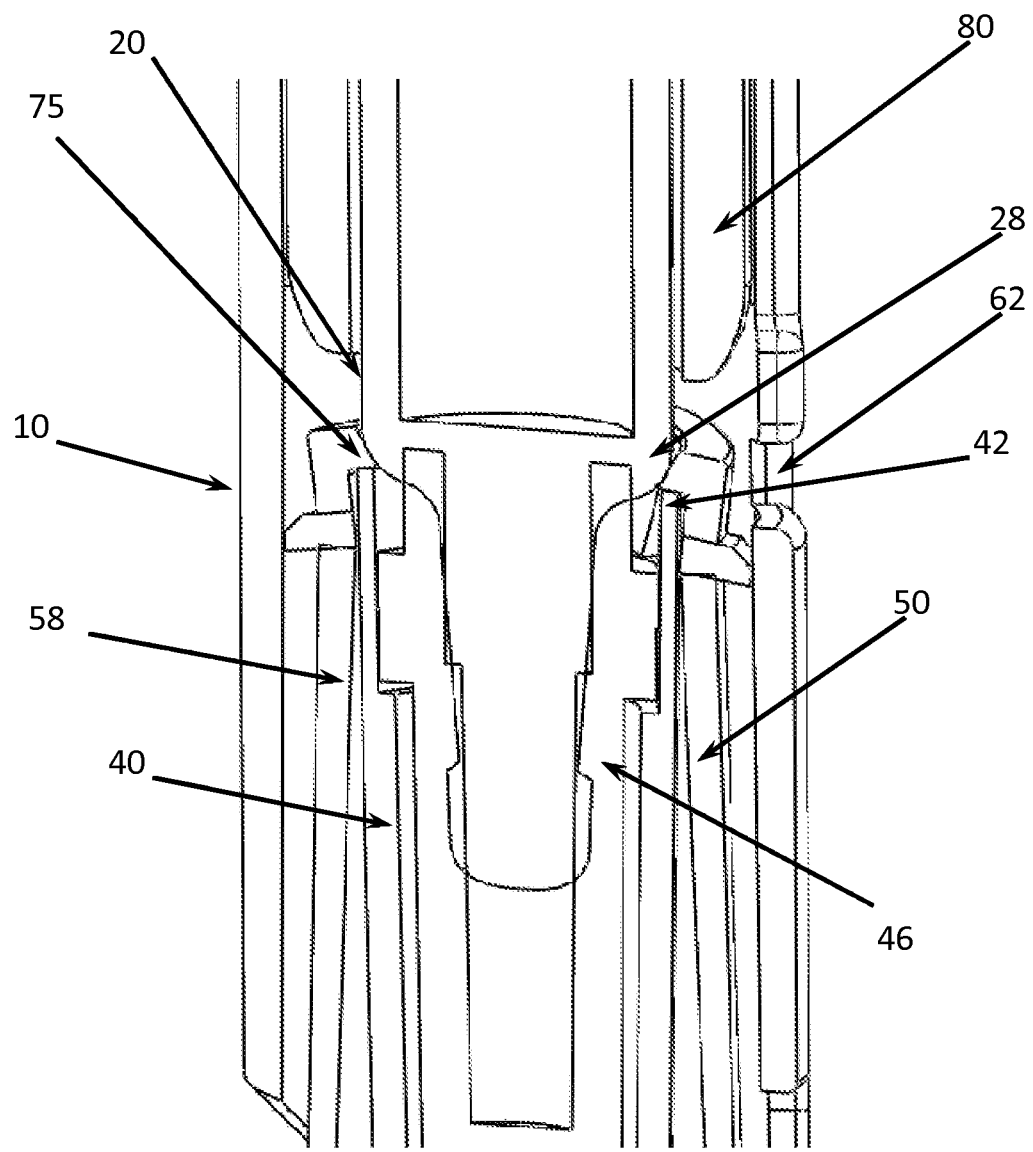
FIG. 22 illustrates the alternate embodiment from FIGS. 20 and 21 after the RNS removal tool has begun moving axially in a distal direction away from the syringe and the RNS removal tool capture lip has captured the RNS.
Figure 23:
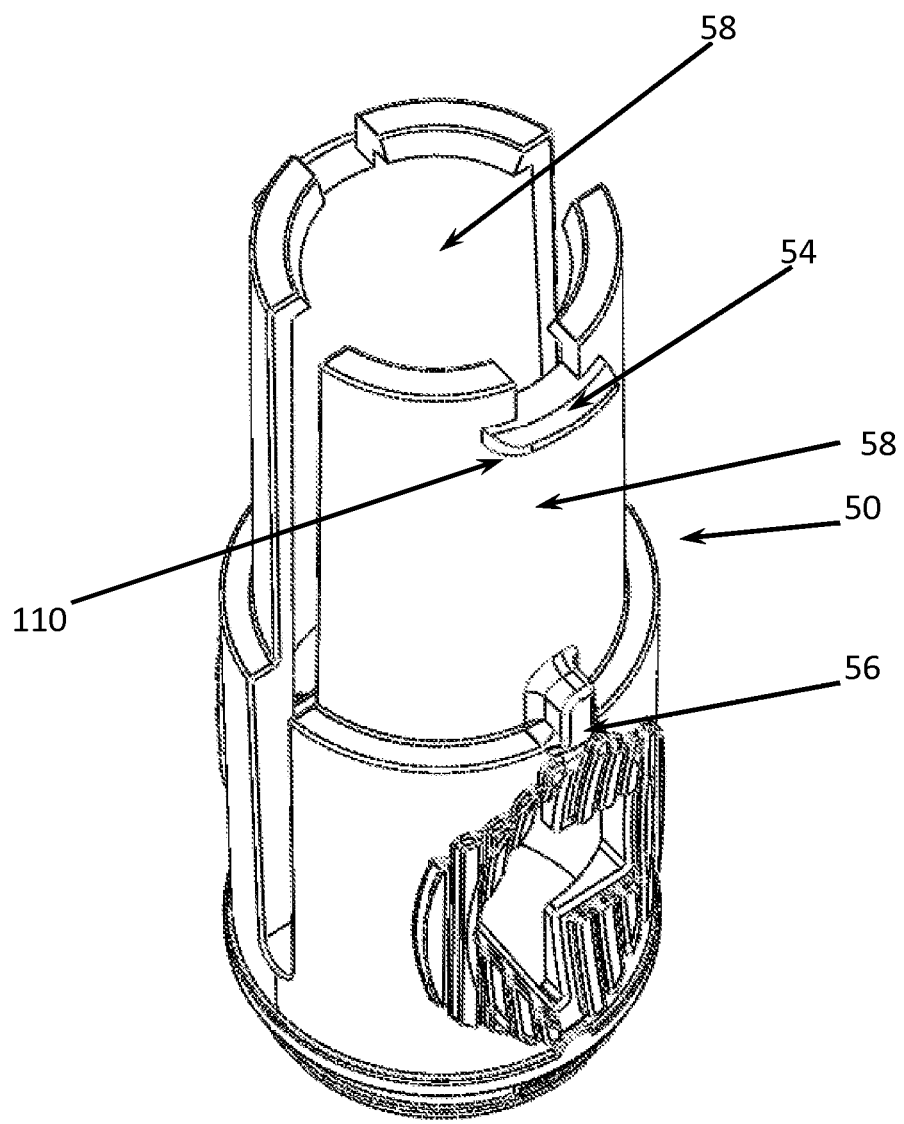
FIG. 23 illustrates the RNS removal tool of the alternate embodiment described in FIG. 20.
Figure 24:
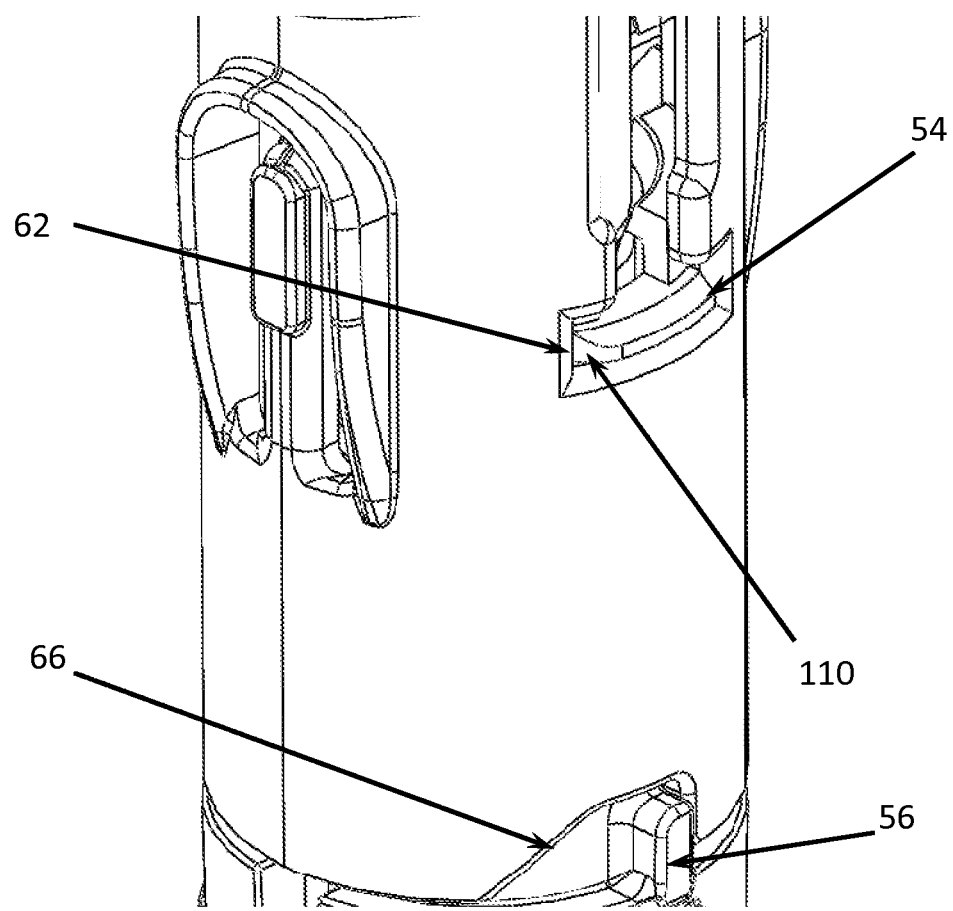
FIG. 24 illustrates the interaction between the RNS removal tool retention barb and its interface with the main body retention window of the alternate embodiment described in FIG. 20.

The mechanical advantage of the barbs 54 engaging the edges of the retention windows 62 provides a strong radial squeeze so that the inwardly projecting capture lips 75 on the RNS removal tool 50 further engages the proximal edge 42 of the RNS 40 as shown in FIGS. 17 and 22. This engagement cannot pre-exist sufficiently since the syringe 20 and RNS 40 must assemble into the device 10, from the proximal to distal end of device 10, with minimal resistance or disturbance to the RNS 40 seal as shown in FIG. 16. After the proximal end 42 of the RNS 40 is engaged by the RNS removal tool 50, the axial cam follower 56 engages a sloped surface 67 of the main body axial cam profile 66 as shown in FIG. 15 which places a mechanically advantaged axial force on the RNS removal tool 50 in a distal direction, creating a distal axial displacement and forming a gap between the main body 60 and the RNA removal tool 50.

Because of the radial and axial cam surface between the RNS removal tool 50 and the main body 60, the RNS removal tool 50 pushes the RNS 40 off of the syringe 20 and needle 24 with much less effort on the part of the user than would normally be required.

Although this description has used a RNS 40 as an example, soft needle shields, which do not have a hard plastic outer shell, could equally be used in this application with minor changes to account for different geometry.

A further improvement to the device could be a distal end cap 158 (FIG. 18A) on the RNS removal tool 50 and a proximal inwardly projecting lip (not shown) that together would help contain the RNS 40 after it had been removed from the syringe 20, preventing it from falling to the floor, etc.

The RNS removal tool 50 can also have large cut-through arrows 51 indicating the direction of rotation to the end user. It could also have large wings 53 extending radially outward to provide greater rotational mechanical advantage for the end user (see FIG. 13).

Figure 18A:
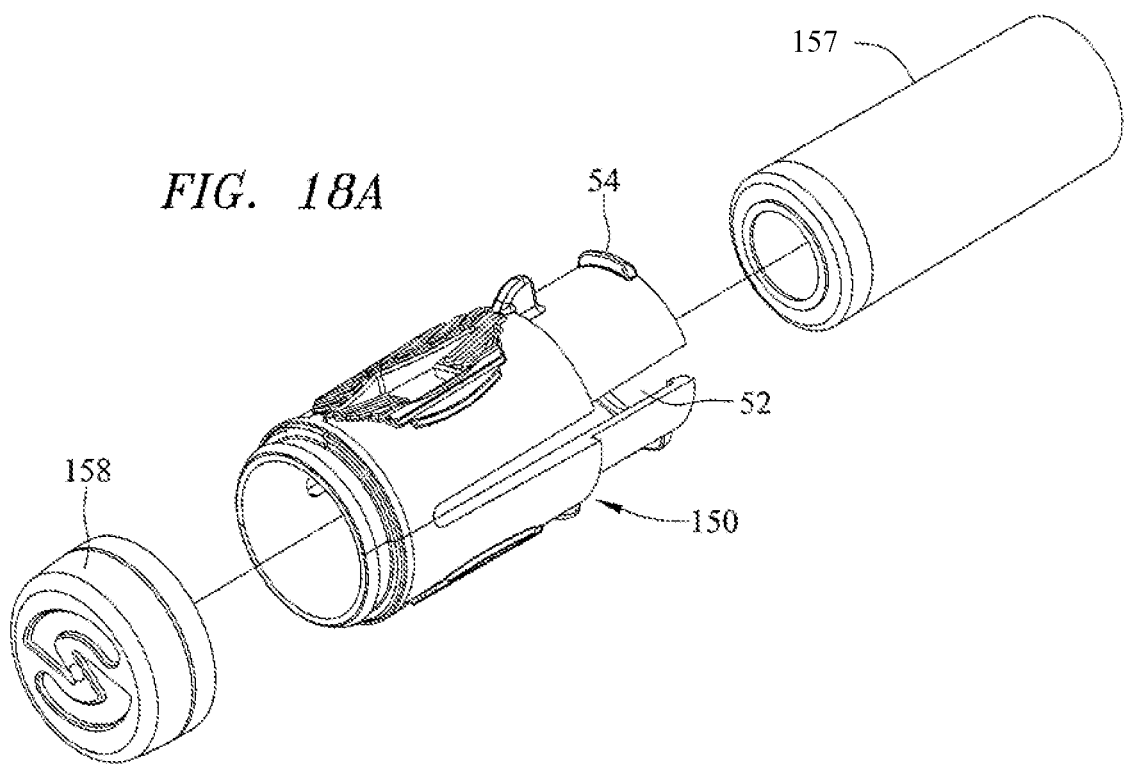
FIG. 18A illustrates an exploded view of another embodiment of the RNS removal tool having a RNS removal tool cap and a RNS removal tool elastomeric insert.
Figure 18B:
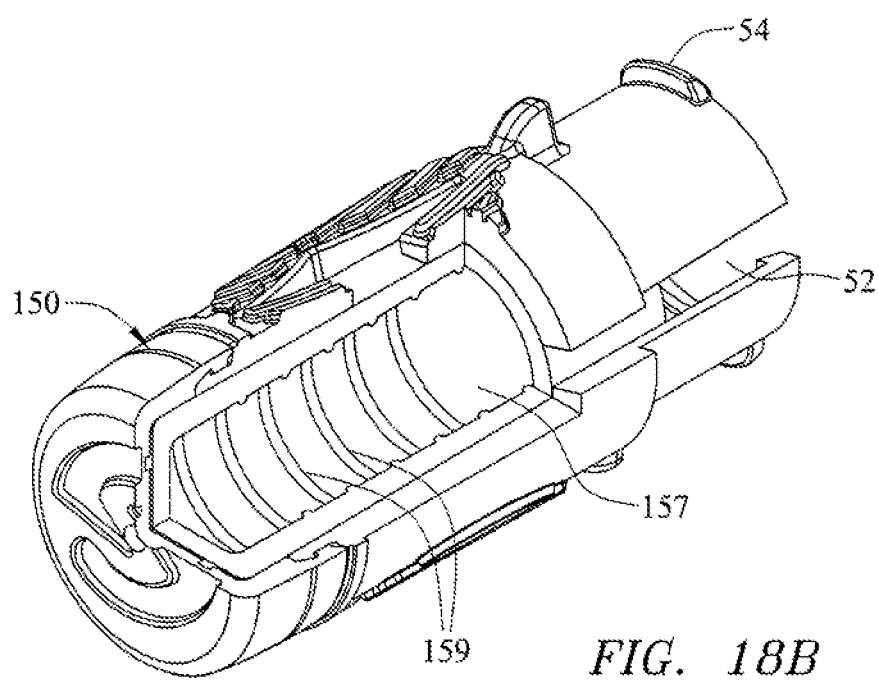
FIG. 18B is a detailed quarter section view showing the alternative embodiment of the RNS removal tool improvement.

The RNS removal tool 50, as described above, pulls the RNS 40 off the syringe/needle 24 by radially collapsing at the proximal end of the RNS 40. When the RNS removal tool 50 has completely pulled the RNS 40 off the syringe/needle 24 and the user relaxes their grip, the collapsed capture of the proximal end of the RNS 40 may no longer be present allowing the RNS 40 to unexpectedly separate and fall from the RNS removal tool 50. An improved version of the RNS removal tool 150 is shown in FIGS. 18A and 18B, wherein an elastomeric insert 157 is placed inside the RNS removal tool 150 such that it nominally has a slight press fit against the RNS 40, the fit being moderate enough to allow for installation of the RNS 40 from the proximal direction during syringe 20 insertion yet sufficient enough to maintain a frictional grip on the RNS 40 to prevent it from separating from the RNS removal tool 150 in the absence of any collapsing grip from the RNS removal tool 150. The size and durometer of the elastomeric insert 157 is such that when the RNS removal tool 150 is rotated as in FIG. 14, the radial squeezing of the RNS removal tool 150 transmits a sufficient squeezing force against the RNS 40 through the elastomeric insert 157 so as to pull the RNS 40 from the syringe/needle 24. Internal circumferential ribs may assist for transmitting a gripping force onto the RNS 40.

Figure 19:
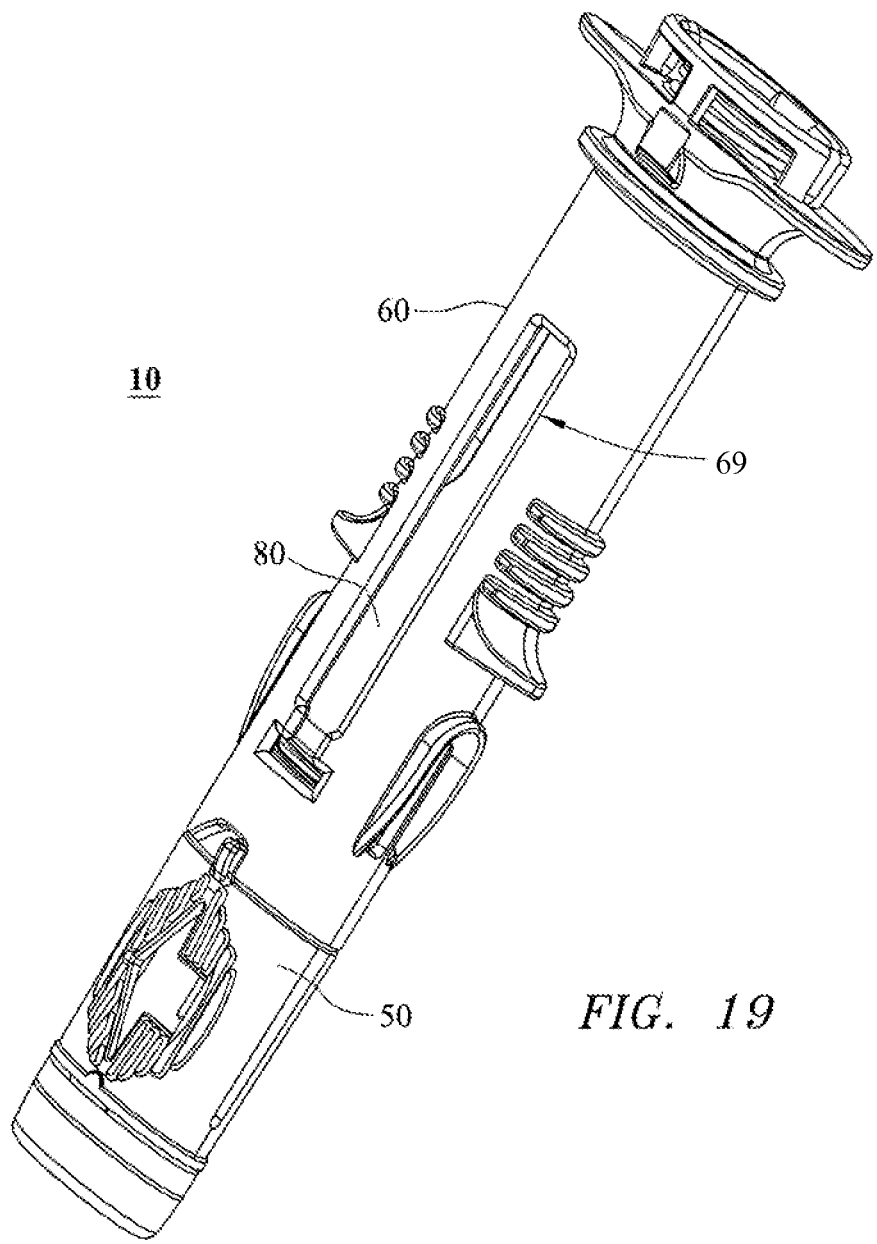
FIG. 19 illustrates another embodiment of the main body window position prior to the removal of the RNS and RNS removal tool.
Figure 20:
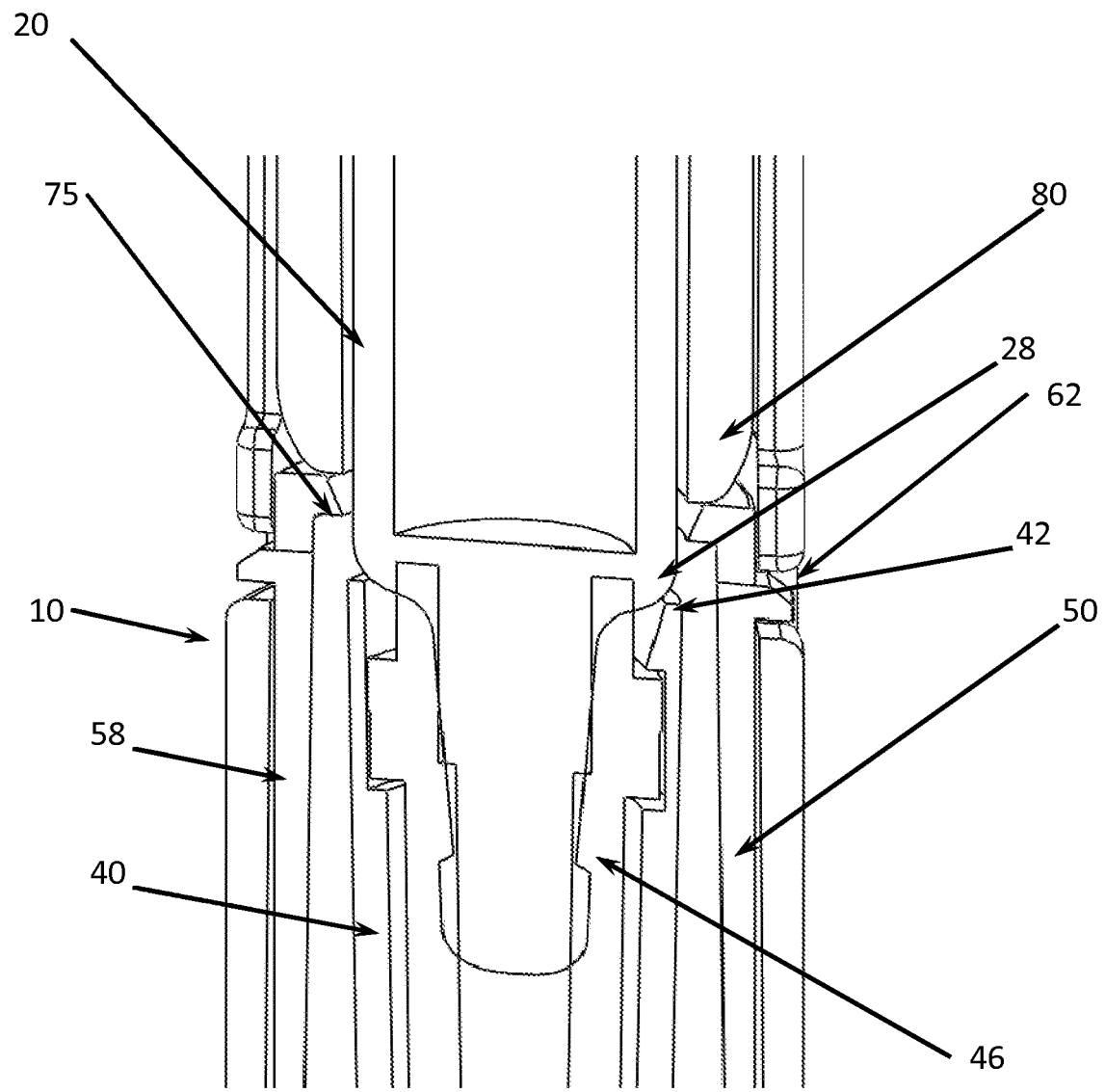
FIG. 20 illustrates an alternate embodiment before the RNS has been removed, where the RNS removal tool is concentric to and positioned around the syringe barrel so that during RNS removal, as the RNS removal tool is rotated, the RNS removal tool capture lip presses against the syringe and not the RNS.

For those applications where full inspection of the syringe drug contents is required before injection, the main body window 69 shown in FIG. 11 can be elongated the amount of the syringe body as shown in FIG. 19. This would also require that the needle guard body 80 be transparent or have a corresponding window since the drug inspection may need to occur before the device is readied for administration.

Figure 25:
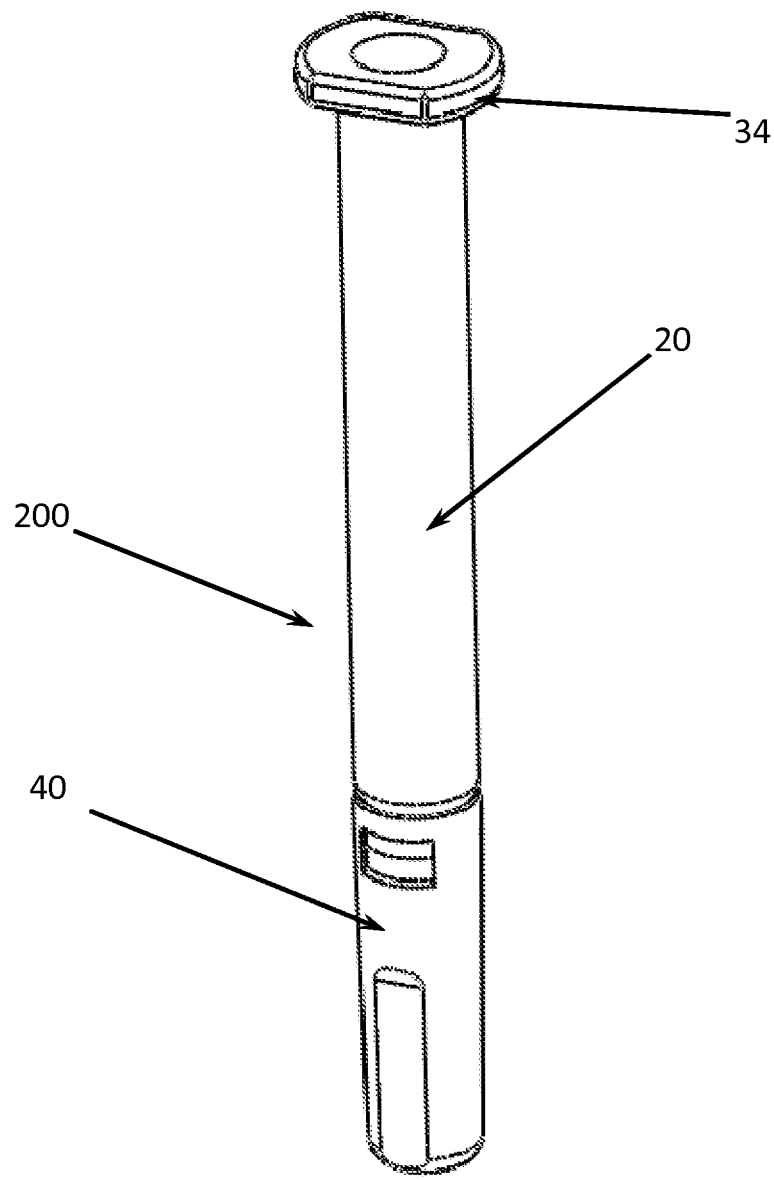
FIG. 25 illustrates the alternate embodiment of the RNS shown in FIG. 20 and syringe subassembly.
Figure 26:
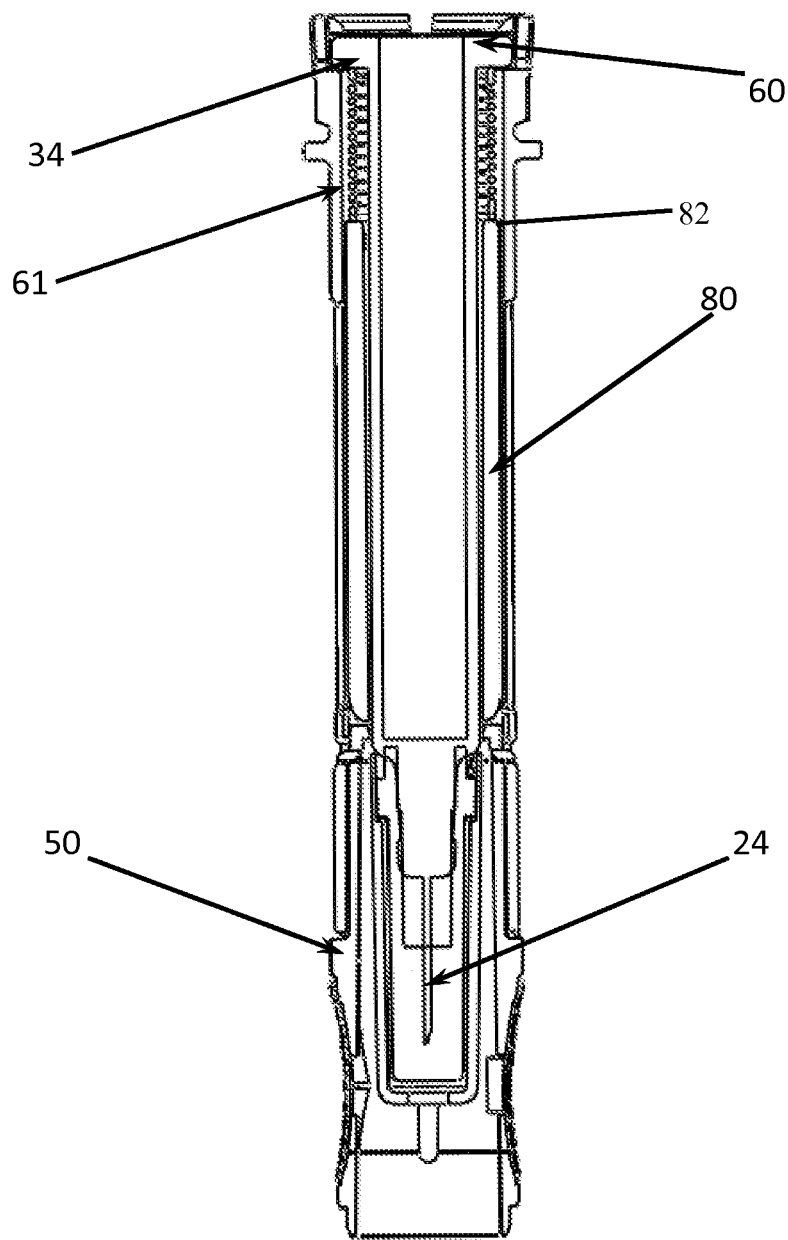
FIG. 26 illustrates a cross sectional view of the alternate embodiment of the RNS shown in FIG. 20 and syringe subassembly.

In an alternate embodiment shown in FIGS. 20-24, the capture lip 75 of the RNS removal tool 50, may come up over the syringe barrel 20 slightly when the device 10 is fully assembled. Consequently, when the RNS removal tool 50 is rotated during rigid needle shield 40 removal, the cam surface 110 on the RNS retention barbs 54, presses against the main body retention window 62, forcing the RNS removal tool arms 58 to press radially inward, causing the RNS removal tool capture lip 75 to press against the barrel of the syringe 20 rather than the RNS 40. This is advantageous during the rotational portion of RNS 40 removal to avoid rotation of the soft needle shield 46 with respect to the syringe needle, which can affect the quality or sharpness of the needle prior to insertion into a patient. In this embodiment, as the RNS removal tool capture lip 75 presses against the barrel of the syringe 20 as it is rotated, the friction created between the two components will impart a force on the barrel of the syringe 20 to encourage rotation of the entire syringe—RNS assembly 200 (FIG. 25). It is expected that either the syringe—RNS assembly 200 will rotate with the RNS removal tool 50, or due to the friction between the syringe flange 34, spring 61, and main body 60 (FIG. 26), the syringe—RNS assembly 200 will remain fixed and the RNS removal tool 50 will rotate around it.

As the RNS removal tool 50 rotates the axial cam follower 56 will encounter the main body axial cam profile 66 forcing the RNS removal tool 50 to move axially away from the syringe 20. Once the axial cam follower 56 on the RNS removal tool 50 reaches the end of the main body axial cam profile 66 the user will be required to continue to pull the RNS removal tool 50 from the device 10, which will be aided by the needle guard body 80, powered by the spring 61.

Figure 21:
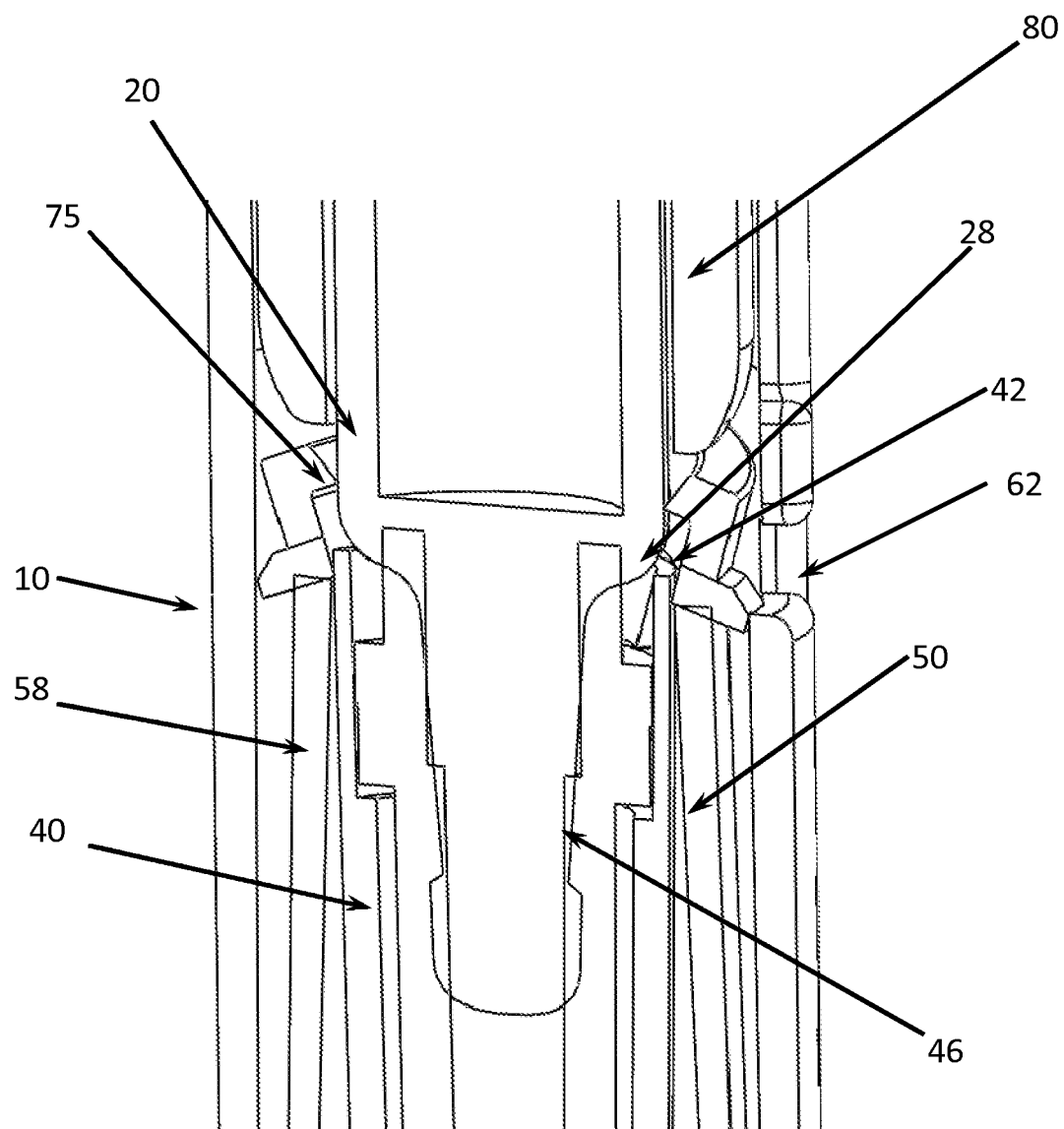
FIG. 21 illustrates the alternate embodiment from FIG. 20 after the RNS removal tool has been rotated and the RNS removal tool capture lips have been pressed against the syringe.

As the RNS removal tool 50 is moving axially away from the syringe 20, the RNS removal tool capture lip 75 will be pressed against the barrel of the syringe 20 (FIG. 21). It will continue to remain in contact with the syringe 20, even as it reaches the syringe neck down area 28. Consequently, the RNS removal tool capture lip 75 will capture the RNS 40 as the RNS removal tool 50 is removed from the device 10 (FIG. 22). By captured, it is meant that the surface of the RNS removal tool capture lips 75 will slide radially inward and over the proximal end surface 42 of the RNS 40. As the RNS removal tool 50 is removed from the device 10 it will pull the RNS 40 axially from the syringe 20, ultimately removing it from the syringe 20.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, unless otherwise stated, and the invention can be performed using different or additional process actions, or a different combination or ordering of process actions. As another example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A needle shield removal tool for use with a needle stick safety device for a syringe, the needle stick safety device including a main body for receiving the syringe, a removable needle shield associated with the main body, and a needle guard slidably engaged with the main body and biased in a distal direction by a biasing member, said needle shield removal tool comprising a covering positionable over the needle shield and removably coupled to the main body, wherein the needle shield removal tool includes one or more axial slits, wherein the needle shield removal tool is configured to retain the needle guard against the bias of the biasing member in a proximal position and wherein removal of the needle shield removal tool is achieved by application of a squeezing force to the needle shield removal tool to cause the needle shield removal tool to collapse along the one or more axial slits, followed by the application of a distal force to the needle shield removal tool to remove the needle shield removal tool and the removable needle shield from the needle stick safety device resulting in the transition of the needle guard from the proximal position to an extended position while remaining engaged with the main body of the needle stick safety device.

2. The needle shield removal tool of claim 1, including barbs configured for cooperating with barb retention windows on the main body.

3. The needle shield removal tool of claim 2, wherein the barbs project outwardly at a proximal end of the needle shield removal tool and mate with the barb retention windows of the main body.

4. The needle shield removal tool of claim 2, including a cam follower for engaging an axial cam of the main body.

5. The needle shield removal tool of claim 1, including an inwardly extending capture lip located at the proximal end of the needle shield removal tool for engaging a proximal end surface of the needle shield upon removal of the needle shield removal tool.

6. The needle shield removal tool of claim 1, including an elastomeric insert having a plurality of ribs.

7. The needle shield removal tool of claim 1, including a distal end cap and a proximal inwardly projecting lip for retaining the removable needle shield therein after removal of the removable needle shield from the syringe.

8. The needle shield removal tool of claim 1, including cut-through arrows on an outer surface thereof indicating a direction of rotation of the needle shield removal tool for removal of the removable needle shield from the syringe.

9. The needle shield removal tool of claim 8, including wings extending radially outward therefrom for assisting in the application of a rotational force to the needle shield removal tool.

10. The needle shield removal tool of claim 1, wherein the main body and needle guard body include diametrically opposed windows which are out of alignment when the needle shield removal tool and removable needle shield are positioned on the syringe and wherein removal of the needle shield removal tool and removable needle shield from the syringe causes the diametrically opposed windows to become aligned.

11. A needle shield removal tool for use with a needle stick safety device for a syringe, the needle stick safety device including a main body for receiving the syringe, a removable needle shield associated with the main body, and a needle guard slidably engaged with the main body and biased in a distal direction by a biasing member, said needle shield removal tool comprising a covering positionable over the needle shield and removably coupled to the main body, wherein the needle shield removal tool is configured to retain the needle guard against the bias of the biasing member in a proximal position and wherein removal of the needle shield removal tool results in the transition of the needle guard from the proximal position to an extended position, the needle shield removal tool including an inwardly extending capture lip located at the proximal end of the needle shield removal tool for engaging a proximal end surface of the needle shield upon removal of the needle shield removal tool wherein the capture lip engages a barrel of the syringe prior to removal of the needle shield removal tool and needle shield from the syringe and wherein application of a distally directed force to the needle shield removal tool causes the capture lip to slide radially inward and over the proximal end surface of the needle shield.

12. A needle shield removal tool for use with a needle stick safety device for a syringe, the needle stick safety device including a main body for receiving the syringe, a removable needle shield associated with the main body, and a needle guard slidably engaged with the main body and biased in a distal direction by a biasing member, said needle shield removal tool comprising a covering positionable over the needle shield and removably coupled to the main body, wherein the needle shield removal tool is configured to retain the needle guard against the bias of the biasing member in a proximal position and wherein removal of the needle shield removal tool results in the transition of the needle guard from the proximal position to an extended position, the needle shield removal tool including barbs configured for cooperating with barb retention windows on the main body and a cam follower for engaging an axial cam of the main body, wherein rotation thereof causes the cam follower to engage a slope edge of the axial cam causing the needle shield removal tool to move axially in the distal direction.

13. The needle shield removal tool of claim 12, wherein rotation thereof causes the barbs to engage the edge of the barb retention windows causing compression of the end of the needle shield removal tool.

14. A needle shield removal tool for use with a needle stick safety device for a syringe, the needle stick safety device including a main body for receiving the syringe, a removable needle shield associated with the main body, and a needle guard slidably engaged with the main body and biased in a distal direction by a biasing member, said needle shield removal tool comprising a covering positionable over the needle shield and removably coupled to the main body, wherein the needle shield removal tool is configured to retain the needle guard against the bias of the biasing member in a proximal position and wherein removal of the needle shield removal tool removes the removable needle shield from the needle stick safety device resulting in the transition of the needle guard from the proximal position to an extended position while remaining engaged with the main body of the needle stick safety device, wherein the needle shield removal tool including radial and axial cam mechanisms.

* * * * *